(12) United States Patent
Manolios

(10) Patent No.: US 7,192,928 B1
(45) Date of Patent: Mar. 20, 2007

(54) T CELL ANTIGEN RECEPTOR PEPTIDES

(75) Inventor: Nicholas Manolios, Kensington (AU)

(73) Assignee: Northern Sydney & Central Coast Area Health Services, Gosford (AU)

( * ) Notice: Subject to any disclaimer, the term of this patent is extended or adjusted under 35 U.S.C. 154(b) by 0 days.

(21) Appl. No.: 09/202,305

(22) PCT Filed: Jun. 11, 1997

(86) PCT No.: PCT/AU97/00367

§ 371 (c)(1),
(2), (4) Date: Mar. 22, 1999

(87) PCT Pub. No.: WO97/47644

PCT Pub. Date: Dec. 18, 1997

(30) Foreign Application Priority Data

| Jun. 11, 1996 | (AU) | PO0389 |
|---|---|---|
| Jun. 11, 1996 | (AU) | PO0390 |
| Jun. 11, 1996 | (AU) | PO0391 |
| Jun. 11, 1996 | (AU) | PO0392 |
| Jun. 11, 1996 | (AU) | PO0393 |
| Jun. 11, 1996 | (AU) | PO0394 |

(51) Int. Cl.
A61K 38/08 (2006.01)
A61K 38/10 (2006.01)

(52) U.S. Cl. .................. 514/14; 514/2; 514/15; 514/16; 514/17; 530/327; 530/328; 530/329; 530/330

(58) Field of Classification Search ............. 514/13, 514/14, 15, 16, 17, 2; 530/326, 327, 328, 530/329, 330
See application file for complete search history.

(56) References Cited

U.S. PATENT DOCUMENTS 5,936,065 A * 8/1999 Arrhenius et al. .......... 530/330

FOREIGN PATENT DOCUMENTS

| EP | 432691 | * | 6/1991 |
|---|---|---|---|
| EP | 0 443 404 | | 8/1991 |
| EP | 0 443 404 A1 | | 8/1991 |
| WO | 91/09613 | * | 7/1991 |
| WO | WO 94/020127 | * | 4/1993 |
| WO | WO 94/20127 | | 9/1994 |
| WO | WO 95/07707 A | | 3/1995 |
| WO | WO 95/26980 | | 10/1995 |
| WO | WO 95/26980 | | 12/1995 |
| WO | WO 95/34312 | | 12/1995 |
| WO | WO 96/03140 A | | 2/1996 |
| WO | WO 96/22306 | | 7/1996 |

OTHER PUBLICATIONS

Ngo et al., 'Computational Complexity, Potein Structure Prediction, and the Levinthal Paradox,' The Protein Folding Problem and Tertiary Structuer Prediction. Ed. K. Merz and L. Le Grand. BirkHauser, Boston MA. pp. 491-495. 1994.*

Rudinger, J. (1976). Peptide Hormones (ed. J.A. Parsons). University Park Press. Baltimore. pp. 1-7.*

Kagan et al. 'Influence of Sequence and Charge on the Specificity of Lysyl Oxidase Toward Protein and Synthetic Peptide Substrate', J. Of Biol. Chem. vol. 259, No. 18, pp. 11203-11207, Sep. 1984.*

Supplemental Euroean Search Report EP 97 92 4813.

Vijay K. Kuchroo et al., "A Single TCR Antagonist Peptide Inhibits Experimental Allergic Encephalomyelitis Mediated by a Diverse T Cell Repertoire", The Journal of Immunology, The Williams and Wilkins Co., Baltimore, US, vol. 153, No. 7, Oct. 1, 1994, pp. 3326-3336.

Stephen C. Jameson et al., "Clone-specific T Cell Receptor Antagonists of Major Histocompatibility Complex Class I-restricted Cytotoxic T Cells", Journal of Experimental Medicine, Tokyo, Japan, vol. 177, No. 6, Jun. 1, 1993, pp. 1541-1550.

K. Hogquist et al., "T Cell Receptor Antagonist Peptides Induce Positive Selection", Cell, Cell Press, Cambride, NA, US, vol. 76, No. 1, Jan. 14, 1994, pp. 17-27.

Shuji Ikagawa et al., "Single Amino Acid Substitutions on a Japanese Cedar Pollen Allergen (Cry⌋ 1)- derived Peptide Induced Alterations in Human T Cell Responses and T Cell Receptor Antagonism", Journal of Allergy and Clinical Immunology, Mosby—Yearly Book, Inc. US, vol. 97, No. 1, part 1, Jan. 1996, pp. 53-64.

Geoffrey A. Cole et al., "T Cell Recognition of the Immunodominant Sendai virus NP324-332/Kb epitope is focused on the center of the Peptide", Journal of Immunology, Coden: JOIMA3; ISSN: 0022-1767, vol. 155, No. 6, Sep. 15, 1995, pp. 2841-2848.

M. Oldstone et al., "Discriminated selection among viral peptides with the appropriate anchor residues: Implications for the size of the cytotoxic T-lymphocyte repertoire and control of viral infection", Journal of Virology, The American Society for Microboiology, U.S. vol. 69, No. 12, Dec. 1, 1995, pp. 7423-7429.

(Continued)

Primary Examiner—Anish Gupta
(74) Attorney, Agent, or Firm—Foley & Lardner LLP

(57) ABSTRACT

The present invention provides peptides which affect T-cells, presumably by action on the T-cell antigen receptor. The present invention further relates to the therapy of various inflammatory and autoimmune disease states involving the use of these peptides. Specifically, the peptides are useful in the treatment of disorders where T-cells are involved or recruited. In one aspect the peptides have the formula: R1-A—B—A—R2 in which A is a hydrophobic amino acid or a hydrophobic peptide sequence comprising between 2 and 10 amino acids; B is a charged amino acid; R1 is NH2 and R2 is COOH. In another aspect the peptides have the formula: R1-A—B—C—R2 in which A is a peptide sequence of between 0 and 5 amino acids; B is cysteine; C is a peptide sequence of between 2 to 10 amino acids; R1 is NH2; and R2 is COOH.

8 Claims, 21 Drawing Sheets

OTHER PUBLICATIONS

Figure 1A:
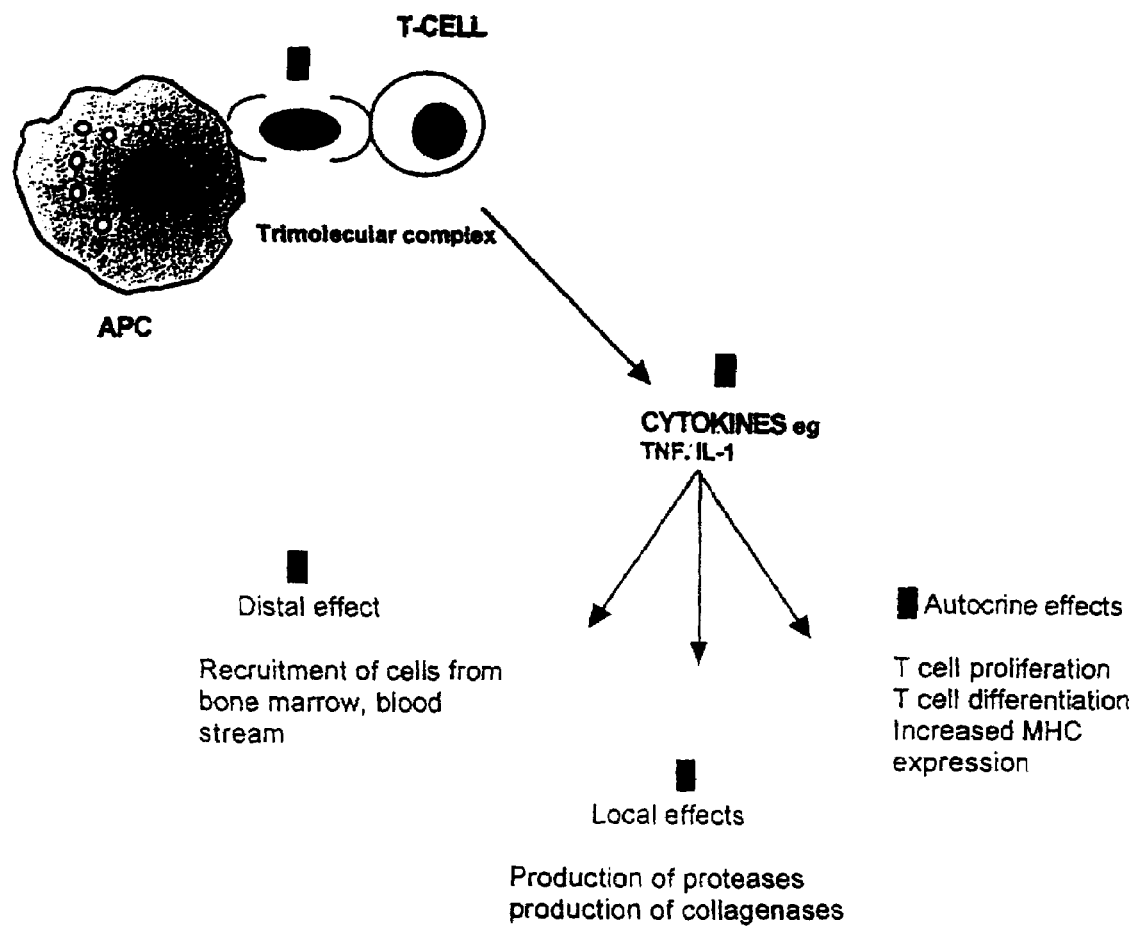

Nathan Karin et al., "Reversal of Experimental Autoimmune Encephalomyelitis by a Soluble Peptide Variant of a Myelin Basic Protein Epitope: T Cell Receptor Antagonism and Reduction of Interferon Gamma and Tumor Necrosis Factor Alpha Production", Journal of Experimental Medicine, Tokyo, JP, vol. 180, No. 6, Dec. 1, 1994, pp. 2227-2237.

M. Teresa De Magistris et al., "Antigen Analog-Major Histocompatibility Complexes Act As Antagonists of the T Cell Receptor", Cell, vol. 68, No. 4, Feb. 21 1992, pp. 625-634.

N.S. Shimizu et al., "Inhibition of infection of T-cells with human immunodeficiency virus type 1 by dideoxynucleosides conjugated with oligopeptides", Antiviral Chemistry and Chemotherapy (1995) 6(1), pp. 17-24.

Bernard Mari et al., "Thrombin and trypsin-induced Ca2+ mobilization in human T cell lines through interaction with different protease-activated receptors", FASEB Journal, CODEN: FAJOEC: ISSN: 0892-6638, vol. 10, No. 2, Feb. 1996, pp. 309-316.

Bjorn R. Gundlach et al., "Determination of T cell epitomes with random peptide libraries", Journal of Immunological Methods, CODEM: JIMMBG; ISSN: 0022-1759, vol. 192, No. 1-2, Jun. 10, 1996, pp. 149-155.

Thomas C. Manning et al., "A strategy for the synthesis and screening of thiol-modified peptide variants recognized by T cells", Journal of Immunological Methods, CODEN: JIMMBG; ISSN: 0022-1759, vol. 192, No. 1-2, Jun. 10, 1996, pp. 125-132.

Irma Joosten et al., "Direct binding of autoimmune diseases related T cell epitopes to purified Lewis rat MHC class II molecules", International Immunology, CODEN: INIMEN; ISSN: 0953-8178, vol. 8, No. 5, May 1994, pp. 751-759.

Peter G. Livingston et al., "Dengue virus-specific, HLA-B35-restricted, human CD8+ cytotoxic T lymphocyte (CTL) cloes. Recognition of NS3 amino acids 500 to 508 by CTL clones. Recognition of NS3 amino acids 500 to 508 by CTL clones of two different serotype specificities", Journal of Immunology, CODEN: JOIMA3; ISSN: 0022-1767, vol. 154, No. 3, Feb. 1, 1995 pp. 1287-1295.

Manolios et al. "T-cell Antigen Receptor Transmembrane Peptide Modulate T-cell Function and T-cell Mediated Disease" *Nature Medicine* 3(1):84-88, Jan. 1997.

International Search Report.

Vijay K. Kuchroo et al., "A Single TCR Antagonist Peptide Inhibits Experimental Allergic Encephalomyelitis Mediated by a Diverse T Cell Repertoir", The Journal of Immunology, The Williams and Wilkins Co., Baltimore, US, vol. 153, No. 7, Oct. 1, 1004, pp. 3326-3336.

S.C. Jameson et al., "Clone-Specific T Cell Receptor Antagonists of Major Histocompatibility Complex Class I-Restricted Cytotoxic T Cells", Journal of Experimental Medicine, Tokyo, Japan, vol. 177, No. 6, Jun. 1, 1993, pp. 1541-1550.

K.A. Hogquist et al., "T Cell Receptor Antagonist Peptides Induce Positive Selection", Cell, Cell Press, Cambridge, NA, US, vol. 76, No. 1, Jan. 14, 1994.

N. Karin et al., "Reversal of Experimental Autoimmune Encephalomyelitis by a Soluble Peptide Variant of a Myelin Basic Protein Epitope: T Cell Receptor Antagonism and Reduction of Interferon Gamma and Tumor Necrosis Factor Alpha Production", Journal of Experimental Medicine, Tokyo, JP, vol. 180, No. 6, Dec. 1, 1994, pp. 2227-2237.

M. T. De Magistris et al., "Antigen Analog-Major Histocompatiblity Complexes Act as Antagonists of the T Cell Receptor", CELL, vol. 68, No. 4, Feb. 21, 1992, pp. 625-634.

* cited by examiner

T CELL ANTIGEN RECEPTOR PEPTIDES

FIELD OF INVENTION

The present invention relates to novel peptides designed to interfere with the function of the T-cell, such that the novel peptide can be used in the treatment of various inflammatory and autoimmune disease states. In particular, the peptide is useful in the treatment of disorders where T-cells are involved or recruited.

BACKGROUND AND INTRODUCTION TO INVENTION

T Cell Receptor Assembly

T-cells are a subgroup of cells which together with other immune cell types (polymorphonuclear, eosinophils, basophils, mast cells, B-, NK cells), constitute the cellular component of the immune system. Under physiological conditions T-cells function in immune surveillance and in the elimination of foreign antigen. However, under pathological conditions there is compelling evidence that T-cells play a major role in the causation and propagation of disease. In these disorders, breakdown of T-cell immunological tolerance, either central or peripheral is a fundamental process in the causation of autoimmune disease.

Central tolerance involves thymic deletion of self reactive cells (negative selection) and positive selection of T-cells with low affinity for self major histocompatibility complex antigens (MHC). In contrast, there are four, non-mutually exclusive hypotheses that have been proposed to explain peripheral T-cell tolerance which are involved in the prevention of tissue specific autoimmune disease. These include: anergy (loss of co-stimulatory signals, down regulation of receptors critical for T-cell activation), deletion of reactive T-cells, ignorance of the antigen by the immune system and suppression of autoreactive T-cells. Tolerance once induced does not necessarily persist indefinitely. A breakdown in any of these mechanisms may lead to autoimmune disease.

Autoimmune disease and other T-cell mediated disorders are characterised by the recruitment of T-cells to sites of inflammation. T-cells at these sites, coupled with their ability to produce and regulate cytokines and influence B-cell function, orchestrate the immune response and shape the final clinical outcome. An understanding of the process of T-cell antigen recognition and subsequent T-cell activation, leading to T-cell proliferation and differentiation, is therefore pivotal to both health and disease. Disturbance in this intricate structure-function relationship of the T-cell antigen receptor, harmonising antigen recognition with T-cell activation may provide the therapeutic means to deal with inflammation and T-cell mediated disorders.

The TCR is composed of at least seven transmembrane proteins[1]. The disulfide-linked (αβ-Ti) heterodimer forms the monotypic antigen recognition unit, while the invariant chains of CD3, consisting of ε, γ, δ, and ζ and η chains, are responsible for coupling the ligand binding to signalling pathways that result in T-cell activation and the elaboration of the cellular immune responses. Despite the gene diversity of the TCR chains, two structural features are common to all known subunits. Firstly, they are transmembrane proteins with a single transmembrane spanning domain—presumably alpha-helical. Secondly, all the TCR chains have the unusual feature of possessing a charged amino acid within the predicted transmembrane domain. The invariant chains have a single negative charge, conserved between the mouse and human, and the variant chains possess one (TCR-β) or two (TCR-α) positive charges. Listed in Table 1 is the transmembrane sequence of TCR-α in a number of species showing that this region is highly conserved and that phylogenetically may subserve an important functional role. The octapeptide (bold) containing the hydrophilic amino acids arginine and lysine is identical between the species. The amino acid substitutions noted in the remaining portions of the transmembrane sequence are minor and conservative.

TABLE 1

Sequence comparison of TCR-α transmembrane region in several species

| SPECIES | SEQUENCE | |
|---|---|---|
| MOUSE | NLSVMGLRILLLKVAGFNLLMTL | SEQ ID NO. 1 |
| RAT | NLSVMGLRILLLKVAGFNLLMTL | SEQ ID NO. 2 |
| SHEEP | NLSVTVFRILLLKVVGFNLLMTL | SEQ ID NO. 3 |
| COW | NLSVI VFRILLLKVVGFNLLMTL | SEQ ID NO. 4 |
| HUMAN | NLSVI GFRILLLKVAGFNLLMTL | SEQ ID NO. 5 |

Studies on the assembly of the multicomponent TCR by Manolios et al[2,3,4] showed that the stable interaction between TCR-α and CD3-δ and TCR-α and CD3-ε was localised to eight amino acids within the transmembrane domain of TCR-α and it was the charged amino acids arginine and lysine that were critical for this process. This finding exemplified the fact that amino acids within the transmembrane domain not only functioned to anchor proteins but were important in the assembly of subunit complexes and protein—protein interactions. For the first time it was found that the assembly of this complex receptor could hinge on only eight amino acids. The above system depended on the modification of complementary strand DNA (cDNA) to create a number of protein mutants. Chimeric cDNA molecules were transfected into COS cells to express the required protein. Coexpression of these chimeric proteins were used to evaluate the region of interaction. The technology involved cDNA manipulation, metabolic labelling, immunoprecipitation and gel electrophoresis. Transmembrane domains are small in size and proteins transversing this region are constrained to an alpha-helical configuration. These biophysical features coupled with the ability to engineer protein—protein interactions via transmembrane charge groups suggested a possible new approach to intervene and potentially disturb TCR function. The use of peptides as possible inhibitors of assembly, the recognition and application of this peptide sequence as a possible therapeutic agent to interfere with T-cell function was not a normal or obvious extension.

In co-pending International Patent Application No. PCT/AU96/00018 the present inventor developed peptides which disturb TCR function. The disclosure of this application is included herein by cross-reference[5].

Biologics in the Treatment of Inflammatory Disease.

In the last decade a new age of therapeutics has developed with the so-called "Biologics", that aim to target specific individual cells, and molecules within the cells, with the specific purpose of interrupting immunological networks and cascades thought to underlie the disease process. The disease model for rheumatoid arthritis has been exemplary in the design of biological agents and a number of different approaches have been devised and tested[6]. The model predicts that an initial arthritogenic peptide is presented to T-cells by an antigen presenting cell (APC) which causes activation of T cells and release of cytokines and proteases culminating in chronic inflammation and joint damage (FIG. 1a). Based on this model a large number of different potentially therapeutic strategies have been devised and used to interfere with the interaction between TCR, MHC and antigen (trimolecular complex) and thereby influence the immune response. Early therapeutic attempts at reducing circulating lymphocyte numbers, included nodal irradiation[7], thoracic duct drainage[8] and lymphocytapheresis[9]. Newer sites of lymphocyte intervention are numbered (1–5) in FIG. 1a and include the use of monoclonal antibodies (MAbs) to either delete T-cells or regulate their function, T-cell vaccines against the pathogenic T-cells, the synthesis of analogous peptides to compete with the antigenic peptide, and inhibition of cytokine action following T-cell activation. These new immunomodulatory therapeutic approaches have been applied in animal models, of spontaneously or experimentally induced autoimmune disease, with encouraging results. These approaches are now being used in human autoimmune diseased. More novel approaches focus on eliminating or modulating T-cells by interfering with the delicate trimolecular complex between antigen, T-cell and MHC molecules. Since antigen is recognised by B and/or T cells and subsequent events are based on this interaction, we have reasoned that interfering with the early antigen recognition events (trimolecular complex) may have profound effects on the development of disease, irrespective of what downstream cellular and cytokine events may occur.

Figure 1B:
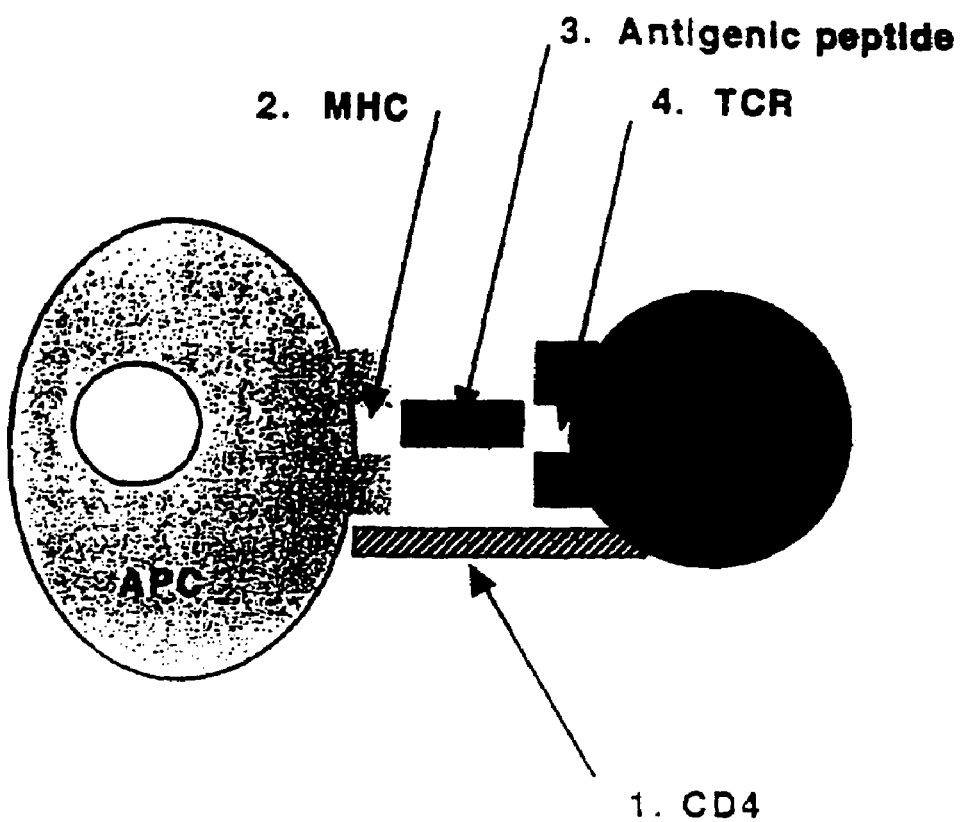

The trimolecular complex as the site for therapeutic intervention has been the subject of focus since the recent advances in the molecular characterisation of its constituents and has provided several approaches for immune intervention. The aim of therapy is to eliminate, prevent or down-regulate the T-cell response by a variety of means (FIG. 1b).

(i) MAbs to T-cell antigens. The use of MAbs in the treatment of RA has been reviewed by a number of authors[6, 10, 11]. The MAbs tested were directed against a variety of antigens ranging from: (a) those present on all mature T-cells, and thought to be involved in the pathogenesis of RA (CD5, CDw52)[12, 13]; (b) MAbs specific for T-cell subsets (CD4), which have the advantage of limited immunosuppressive effects[14,15]; and (c) to MAbs directed against T-cell activation antigens (IL-2 receptor) which may specifically suppress activated T-cells in response to antigen[16,17]. All the MAbs used are derived from rodents and only CAMPATH-1H has been "humanised" by recombinant cDNA techniques. Clinical studies indicate that these MAbs are well tolerated in patients and can induce a favourable clinical response. Side effects include an immune reaction to the rodent antibodies which may restrict recurrent use.

(ii) Anti-MHC therapy. Immunogenetic studies have demonstrated that the MHC molecules (DR1, DR4, Dw4 and DR4 Dw14) are important in RA susceptibility[18]. Since MHC molecules present antigenic peptides to T-cells they provide another target for immune intervention. The function of these molecules can be interfered with either by using MAbs (to the antigen binding sites)[19] or high affinity binding of competitor peptides to the MHC groove (see below). MAbs directed against MHC molecules interfere with disease initiation in several animal models of autoimmunity[20, 21] and humans[22].

(iii) Peptide competition. T-cell recognition of antigen can be disrupted by using high affinity MHC-binding peptides which block the antigen-binding site of MHC molecules and inhibit T-cell responses. By substitution of particular amino acid residues it is possible to generate "designer' peptides, which have high affinity for MHC molecules but do not activate T-cells[23]. This therapy has the advantage of specificity without causing generalised immunosuppression.

(iv) T-cell vaccination. This form of therapy holds promise for those diseases which exhibit T-cell oligoclonality. The idea is to obtain pathogenic T-cell clones and vaccinate against these cells hoping to eliminate them from the available T-cell repertoire. Another more refined method of vaccination has been to synthesize peptides corresponding to the T-cell receptor sequences which are involved in antigen recognition. Autoimmune animal models vaccinated with such peptides support the view that it is possible to block functional T-cell clones by using synthetic peptides[24,25]. Whether these antiTCR strategies are applicable to rheumatoid disease depends on the oligoclonality of the autoreactive cells and their limited TCR usage. Although still controversial, evidence of a limited repertoire of TCR usage has been reported in RA[26,27].

(v) Cytokine therapy. Synovial fluid analysis of patients with RA has shown the presence of a large number of cytokines including granulocyte-macrophage colony stimulating factor (GM-CSF), gamma-interferon (IFN-γ), interleukin-1 (IL-1) and tumour necrosis factor (TNF-α)[28]. Cytokines interact with cells to co-ordinate the immune and inflammatory response. They can be grouped as either pro-inflammatory or anti-inflammatory. IL-1 and TNFα are in the former group and act synergistically. TNF-α is also one of the major cytokines regulating the expression of IL-1[28]. Because of their central importance attempts to interfere with their regulation or production may have a positive effect on disease outcome[29, 30]. Administration of IL-1 receptor antagonist to rats and mice with arthritis has reduced the severity of joint lesions and is in Phase II studies in human disease. Therapeutic use of MAbs to the IL-2 receptor has transient effects[31]. The receptors for a large group of cytokines have been cloned and sequenced (reviewed by Dower and Sims)[32] and currently under clinical evaluation[33]. It may be that the soluble form of the cytokine receptors may be used to sequester the cytokines by a ligand type interaction and thereby reduce inflammation. Cyclosporin A modulates T-cell cytokine production and when given in several trials has given good clinical response. However the associated nephrotoxicity limits its use[34].

(vi) The ability to disrupt cellular function by the use of peptides derived from protein sequences critical for receptor assembly, has only recently been published[35] and is a new approach for the use of biologics, that could be included into the schema of biological mechanisms of action. That is, the disruption of cellular function by "disorganising" the assembly of receptors by use of peptides. By design, the peptide chosen corresponded to a common transmembrane sequence common to both CD4 and CD8 cells and currently other unique sites of TCR chain interaction are under investigation. In particular, interactions in the extra cellular domain between the antigen recognition chains, may prove useful in devising peptides for individual pathogenic T cell clones with specific Vα/Vβ usage.

DISCLOSURE OF INVENTION

The present inventor has now developed further novel peptides which disturb TCR function, presumably by interfering with assembly. These peptides are based on sequences from (i) the core peptide; (ii) peptides that correspond to alternative chain assembly regions; ie. CD3-δ,-ϵ,-γ chains; (iii) new sites of assembly, ie. interchain disulphide bond; and (iv) downstream sequences of core peptide. The present inventor has also found that these peptides have an effect on T-cell mediated inflammation. The efficacious clinical manifestations of the administered peptide would be a decrease in inflammation, e.g. as demonstrated by a decrease of arthritis in an adjuvant model of arthritis.

Accordingly, in a first aspect the present invention provides a peptide which inhibits TCR function, wherein the peptide is of the following formula:—

R1-A—B—A—R2 in which

A is a hydrophobic amino acid or a hydrophobic peptide sequence comprising between 2 and 10 amino acids
B is a charged amino acid
R1 is NH2 and
R2 is COOH By "hydrophobic peptide sequence" we mean a sequence which includes at least 1 hydrophobic amino acid and which does not include a charged amino acid. Preferably, at least 50% of the amino acids make up the hydrophobic peptide sequence are hydrophobic amino acids. More preferably at least 80% of all amino acids which make up the hydrophobic peptide sequence are hydrophobic amino acids.

In a preferred embodiment of the present invention A is a peptide comprising from 2 to 6 amino acids.

In one preferred embodiment of the present invention the peptide sequence is derived from the TCR-α transmembrane chain. In one preferred aspect of this embodiment B is a positively charged amino acid. B is preferably lysine or arginine.

In yet a further preferred embodiment of the present invention the peptide comprises the sequence NH2-Ile-Leu-Leu-Leu-Lys-Val-Ala-Gly-Phe-OH, (SEQ ID NO. 6)

NH2 Ile-Leu-Leu-Leu-Lys-Val-Ala-Gly-OH, (SEQ ID NO. 7)

NH2-Leu-Arg-Ile-Leu-Leu-Leu-Gly-Val-OH, (SEQ ID NO. 8)

NH2-Leu-Gly-Ile-Leu-Leu-Leu-Lys-Val-OH, (SEQ ID NO. 9)

NH2-Ile-Leu-Leu-Gly-Lys-Ala-Thr-Leu-Tyr-OH (SEQ ID NO. 10) or

NH2-Met-Gly-Leu-Arg-Ile-Leu-Leu-Leu-OH (SEQ ID NO. 11).

In a further preferred embodiment the peptide sequence is derived from the TCR-α intracellular chain. In a preferred aspect of this embodiment the peptide comprises the sequence:

NH2-Leu-Leu-Met-Thr-Leu-Arg-Leu-Trp-Ser-Ser-COOH (SEQ ID NO. 12).

In a further preferred embodiment the peptide sequence is derived from the transmembrane CD3-δ, -ε, or -γ chain sequence. In this preferred embodiment B may be a negatively charged amino acid.

In yet a further preferred embodiment the peptide sequence is derived from the CD3-δ or -ε chain. In this preferred embodiment B may be aspartic acid. In a particularly preferred aspect of this embodiment the peptide comprises the following sequence:—

NH2-Ile-Ile-Val-Thr-Asp-Val-Ile-Ala-Thr-Leu-OH (SEQ ID NO. 13),

NH2-Ile-Val-Ile-Val-Asp-Ile-Cys-Ile-Thr-OH (SEQ ID NO. 14).

In yet a further embodiment the peptide sequence is derived from the CD3-γ chain. In this preferred embodiment B may be glutamic acid. In a particularly preferred aspect of this embodiment the peptide comprises the following sequence:—

NH2-Phe-Leu-Phe-Ala-Glu-Ile-Val-Ser-Ile-OH (SEQ ID NO. 15).

In a second aspect the present invention provides a peptide which inhibits TCR function, wherein the peptide is derived from the TCR-α intracellular chain and comprises the formula:

NH2-Ala-Gly-Phe-Asn-Leu-Leu-Met-Thr-COOH (SEQ ID NO. 16).

It has also been found that the TCR-αβ interchain disulphide bond plays an important role in the T cell assembly and subsequent activation by antigenic peptide.

The present invention therefore also provides novel peptides which destabilise the interchain cysteine bond of the TCR-α and TCR-β chains and inhibit T-cell activation.

Accordingly, in a third aspect the present invention provides a peptide which inhibits TCR function, wherein the peptide is of the following formula:—

R1-A—B—C—R2 in which

A is a peptide sequence of between 0 and 5 amino acids;
B is cysteine;
C is a peptide sequence of between 2 to 10 amino acids;
R1 is NH2; and
R2 is COOH.

In a preferred embodiment of the present invention A is a peptide sequence consisting of 5 amino acids.

In one embodiment the peptide is derived from the TCR-β chain. Preferably, C is a peptide consisting of 4 or 5 amino acids and includes at least one hydrophobic amino acid. In a preferred embodiment the peptide has the following sequence:—

NH2-Tyr-Gly-Arg-Ala-Asp-Cys-Gly-Ile-Thr-Ser-OH (SEQ ID NO. 17),

NH2-Trp-Gly-Arg-Ala-Asp-Cys-Gly-Ile-Thr-Ser-OH (SEQ ID NO. 18), or

NH2-Tyr-Gly-Arg-Ala-Asp-Cys-Ile-Thr-Ser-OH (SEQ ID NO. 19).

In another embodiment the peptide is derived from the TCR-A chain. In this embodiment the peptide preferably has the following sequence:

NH2-Ser-Ser-Asp-Val-Pro-Cys-Asp-Ala-Thr-Leu-Thr-OH (SEQ ID NO. 20).

It will be appreciated by those skilled in the art that a number of modifications may also be made to the peptides of the present invention without deleteriously affecting the biological activity of the peptide. This may be achieved by various changes, such as insertions and substitutions, either conservative or non-conservative in the peptide sequence where such changes do not substantially decrease the biological activity of the peptide.

Modifications of the peptides contemplated herein include, but are not limited to, modifications to side chains, incorporation of unnatural amino acids and/or their derivatives during peptide synthesis and the use of crosslinkers and other methods which impose conformational constraints on the peptides.

Examples of side chain modifications contemplated by the present invention include modifications of amino groups such as by reductive alkylation by reaction with an aldehyde followed by reduction with $NaBH_4$; amidation with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Tryptophan residues may be modified by, for example, oxidation with N-bromosuccinimide or alkylation of the indole ring with 2-hydroxy-5-bitrobenzyl bromide or sulphenyl halides. Tyrosine residues on the other hand, may be altered by nitration with tetranitromethane to form 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid; 2-thienyl alanine and/or D-isomers of amino acids.

The peptides of the present invention may be synthesised using techniques well known to those skilled in this field. For example, the peptides may be synthesised using solution synthesis or solid phase synthesis as described, for example, in Chapter 9 entitled "Peptide Synthesis" by Atherton and Sheppard which is included in a publication entitled "Synthetic Vaccines" edited by Nicholson and published by Blackwell Scientific Publications. Preferably a solid phase support is utilised which may be polystyrene gel beads wherein the polystyrene may be cross-linked with a small proportion of divinylbenzene (e.g. 1%) which is further swollen by lipophilic solvents such as dichloromethane or more polar solvents such as dimethylformamide (DMF). The polystyrene may be functionalised with chloromethyl or anionomethyl groups. Alternatively, cross-linked and functionalised polydimethyl-aclylamide gel is used which may be highly solvated and swollen by DMF and other dipolar aprolic solvents. Other supports can be utilised based on polyethylene glycol which is usually grafted or otherwise attached to the surface of inert polystyrene beads. In a preferred form, use may be made of commercial solid supports or resins which are selected from PAL-PEG, PAK-PEG, KA, KR or TGR.

In solid state synthesis, use is made of reversible blocking groups which have the dual function of masking unwanted reactivity in the α-amino, carboxy or side chain functional groups and of destroying the dipolar character of amino acids and peptides which render them inactive. Such functional groups can be selected from t-butyl esters of the structure RCO—OCMe$_3$—CO—NHR which are known as t-butoxy carboxyl or ROC derivatives. Use may also be made of the corresponding benzyl esters having the structure RCO—OCH$_2$—C$_6$H$_5$ and urethanes having the structure C$_6$H$_5$CH$_2$O CO—NHR which are known as the benzyloxycarbonyl or Z-derivatives. Use may also be made of derivatives of fluorenyl methanol and especially the fluorenyl-methoxy carbonyl or Fmoc group. Each of these types of protecting group is capable of independent cleavage in the presence of one other so that frequent use is made, for example, of BOC-benzyl and Fmoc-tertiary butyl protection strategies.

Reference also should be made to a condensing agent to link the amino and carboxy groups of protected amino acids or peptides. This may be done by activating the carboxy group so that it reacts spontaneously with a free primary or secondary amine. Activated esters such as those derived from p-nitrophenol and pentafluorophenyl may be used for this purpose. Their reactivity may be increased by addition of catalysts such as 1-hydroxybenzotriazole. Esters of triazine DHBT (as discussed on page 215–216 of the above-mentioned Nicholson reference) also may be used. Other acylating species are formed in situ by treatment of the carboxylic acid (i.e. the Na-protected amino acid or peptide) with a condensing reagent and are reacted immediately with the amino component (the carboxy or C-protected amino acid or peptide). Dicyclohexylcarbodiimide, the BOP reagent (referred to on page 216 of the Nicholson reference), O'Benzotriazole-N,N, N'N'-tetra methyl-uronium hexaflurophosphate (HBTU) and its analogous tetrafluroborate are frequently used condensing agents.

The attachment of the first amino acid to the solid phase support may be carried out using BOC-amino acids in any suitable manner. In one method BOC amino acids are attached to chloromethyl resin by warming the triethyl ammonium salts with the resin. Fmoc-amino acids may be coupled to the p-alkoxybenzyl alcohol resin in similar manner. Alternatively, use may be made of various linkage agents or "handles" to join the first amino acid to the resin. In this regard, p-hydroxymethyl phenylactic acid linked to aminomethyl polystyrene may be used for this purpose.

It may also be possible to add various groups to the peptide of the present invention to confer advantages such as increased potency or extended half life in vivo without substantially decreasing the biological activity of the peptide. It is intended that such modifications to the peptide of the present invention which do not result in a decrease in biological activity are within the scope of the present invention.

In a further aspect the present invention provides a therapeutic composition including a peptide of the first, second or third aspect of the present invention and a pharmaceutically acceptable carrier.

In a further aspect the present invention provides a method of treating a subject suffering from a disorder in which T-cells are involved or recruited, the method including administering to the subject a therapeutically effective amount of the peptide of the first, second or third aspect of the present invention.

The therapeutic composition may be administered by any appropriate route as will be recognised by those skilled in the art. Such routes include oral, transdermal, intranasal, parenteral, intraarticular and intraocular.

In further aspect the present invention consists in a method of delivering a chemical moiety to a cell including exposing the cell to the chemical moiety conjugated to a peptide of the first, second or third aspect of the invention.

In a preferred embodiment the chemical moiety is conjugated to the carboxy terminal of the peptide.

A non-exhaustive list of disorders in which T cells are involved/recruited include:
   Allergic diathesis e.g. Delayed type hypersensitivity, contact dermatitis
   Autoimmune disease e.g. SLE, rheumatoid arthritis, multiple sclerosis, diabetes, Guillain-Barre syndrome, Hashimoto's disease, pernicious anaemia Gastroenterological conditions e.g. Inflammatory bowel disease, Chron's disease, primary biliary cirrhosis, chronic active hepatitis Skin problems e.g. psoriasis, pemphigus vulgaris Infective disease e.g. AIDS virus, herpes simplex/zoster Respiratory conditions e.g. allergic alveolitis, Cardiovascular problems e.g. autoimmune pericarditis Organ transplantation Inflammatory conditions e.g. myositis, ankylosing spondylitis Any disorder where T cells are involved/recruited.

As used herein, the term "subject" is intended to cover both human and non-human animals.

The peptides of the present invention may be modified at the carboxy terminal without loss of activity. Accordingly, it is intended that the present invention includes within its scope peptides which include additional amino acids to the "core" sequence of the peptide of the present invention and which affect the T-cell antigen receptor.

It is envisaged that the peptides of the present invention are able to enter cells. Accordingly it is envisaged that, apart from its other uses, the peptide of the present invention could be used as a "carrier" to deliver other therapeutic agents to cells. This could be achieved, for example, by conjugating the therapeutic to be delivered into the cell to the peptide of the present invention.

As will be readily understood by those skilled in this field hydrophobic amino acids are Ala, Val, Leu, Ile, Pro, Phe, Trp and Met; positively charged amino acids are Lys, Arg and His; and negatively charged amino acids are Asp and Glu.

In order that the nature of the present invention may be more clearly understood, preferred forms thereof will now be described with reference to the following examples and figures in which:—

FIG. 1(a)—Schematic representation of antigen recognition by T-cells and subsequent downstream events Possible sites of intervention include the trimolecular complex, T-cells, T-cell surface molecules, cytokines, recruitment of cells, and catalytic enzymes.

FIG. 1(b)—Trimolecular complex with possible intervention sites.

Figure 2:
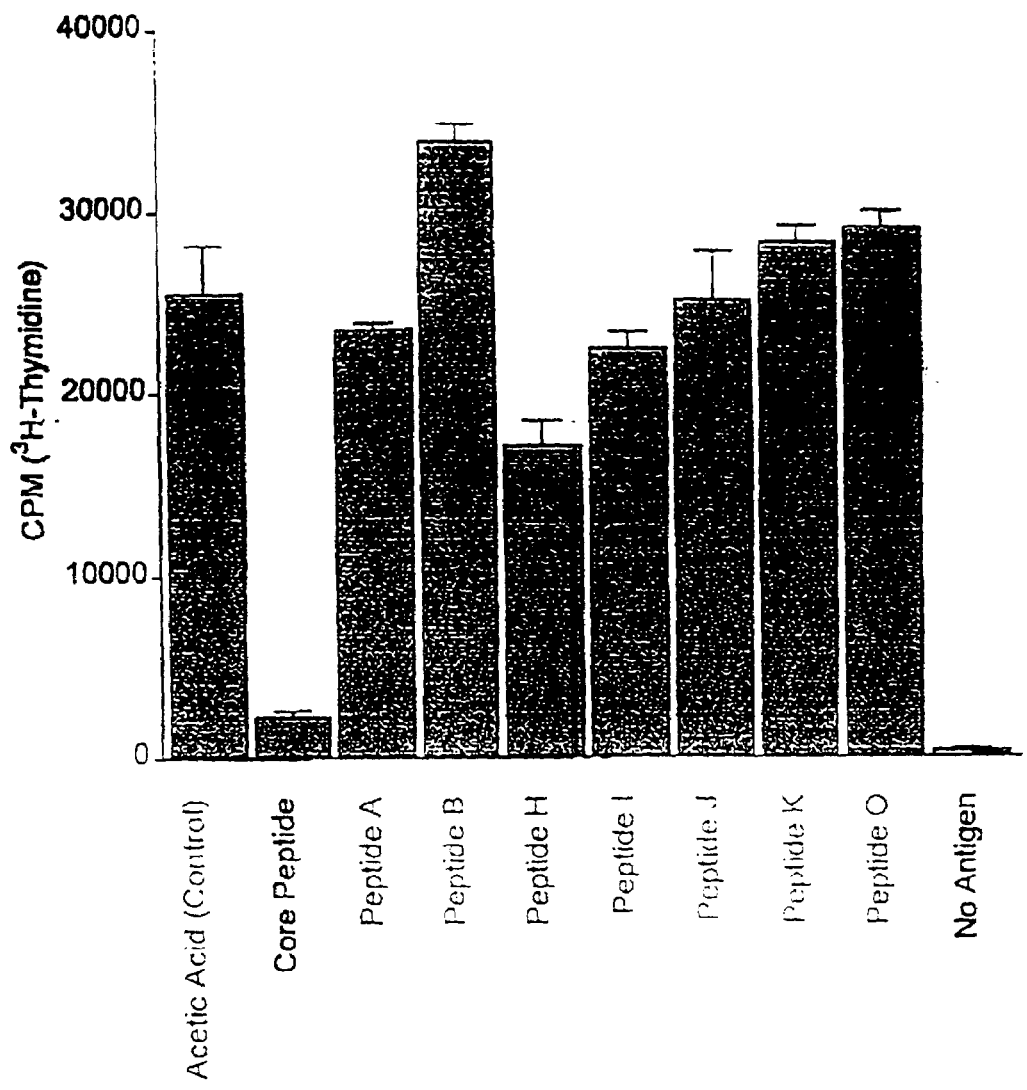

FIG. 2—Effect of peptides on primed lymph node cells. Shown are means and standard errors (n=4). Peptide final concentrations were 100 µg/ml and were delivered to the wells in 20 µl of 0.1% acetic acid.

Figure 3:
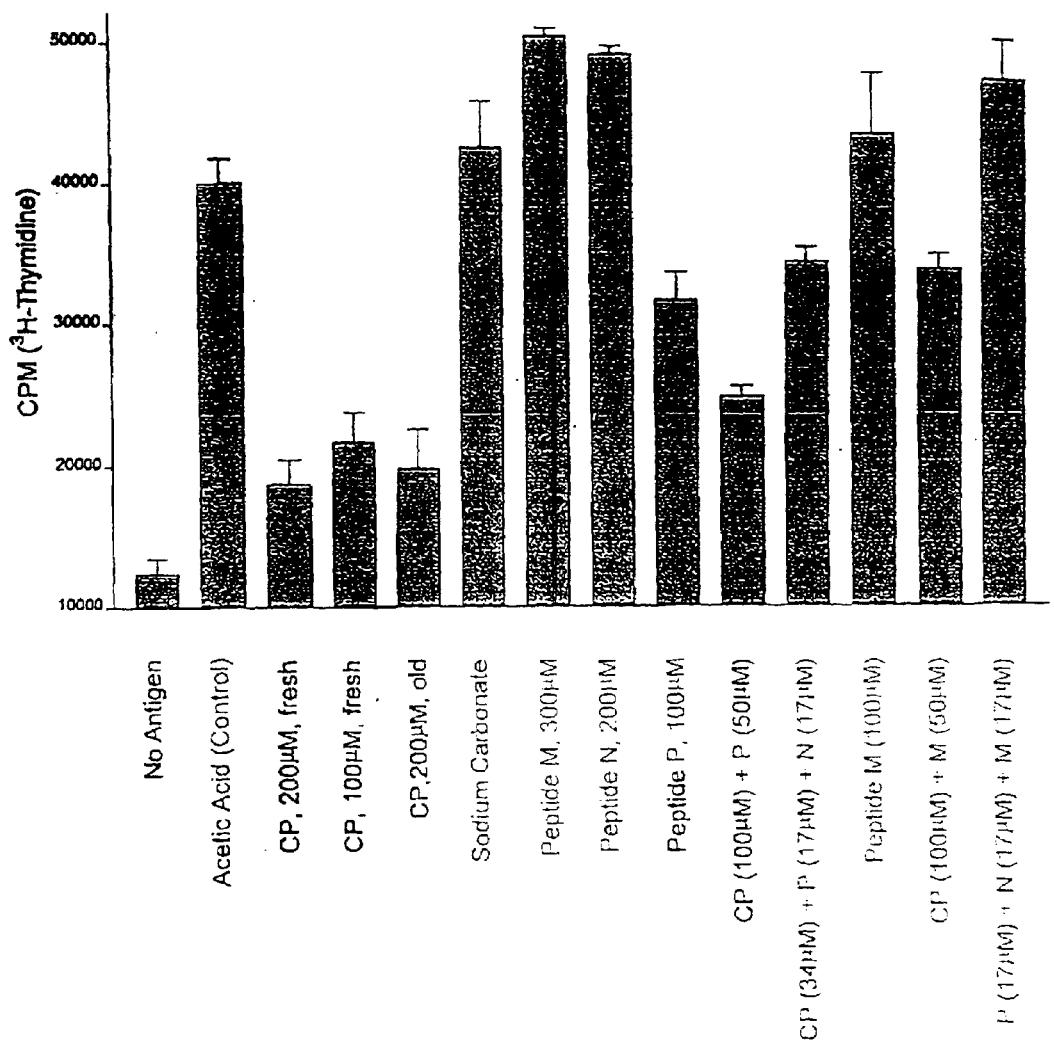

FIG. 3—Effect of peptide/s on primed lymph node cells. Shown are the mean and standard error of four wells. Core peptide (CP) was either freshly dissolved (fresh) or in solution for at least three months at 4° C. (old).

Figure 4:
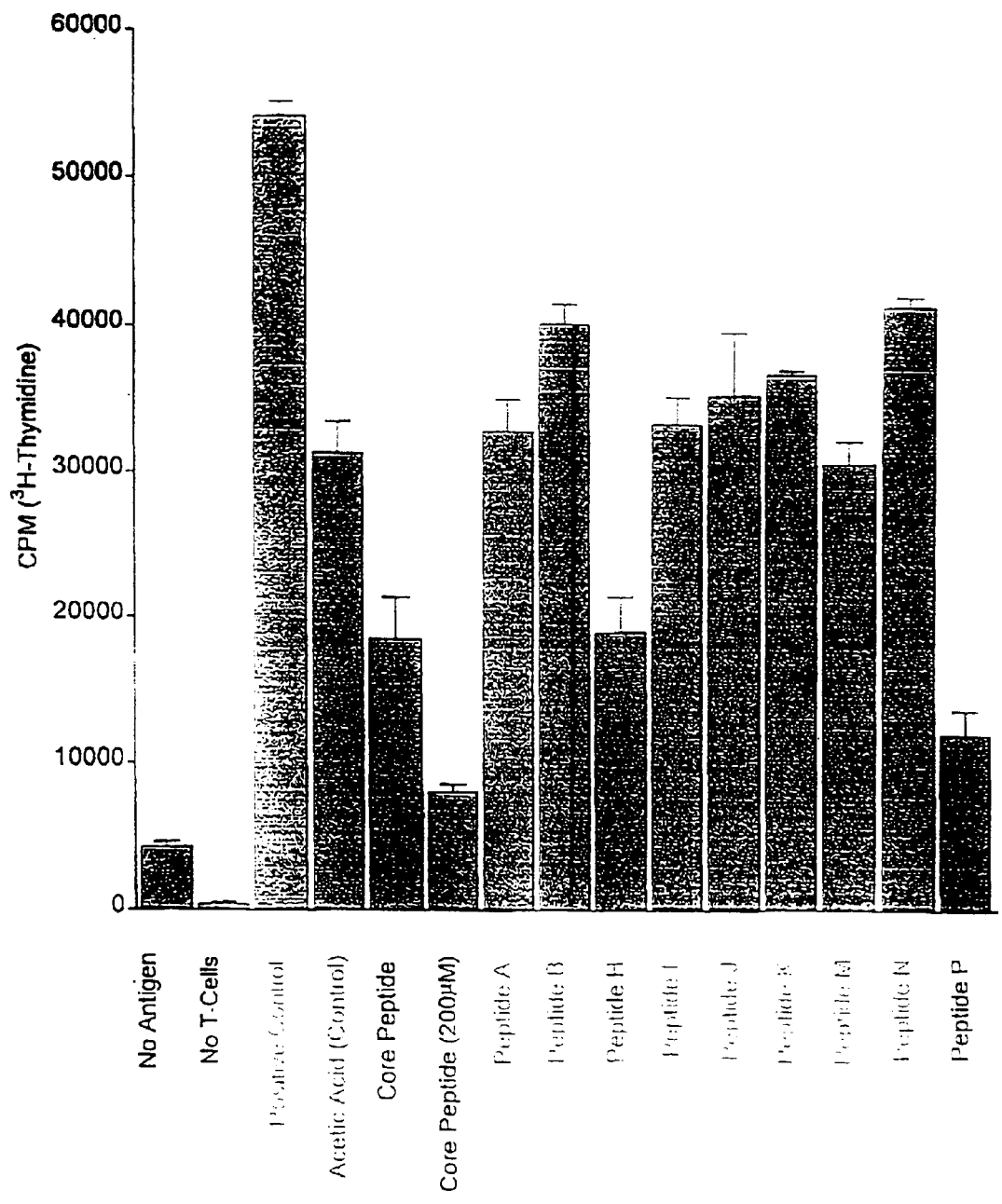

FIG. 4—Effect of peptides on a rat T-cell line specific to MTB. Shown are mean and standard error of four wells. Peptides were 100 µM in the wells and stock solutions were 1 mM in 0.1% acetic acid.

Figure 5:
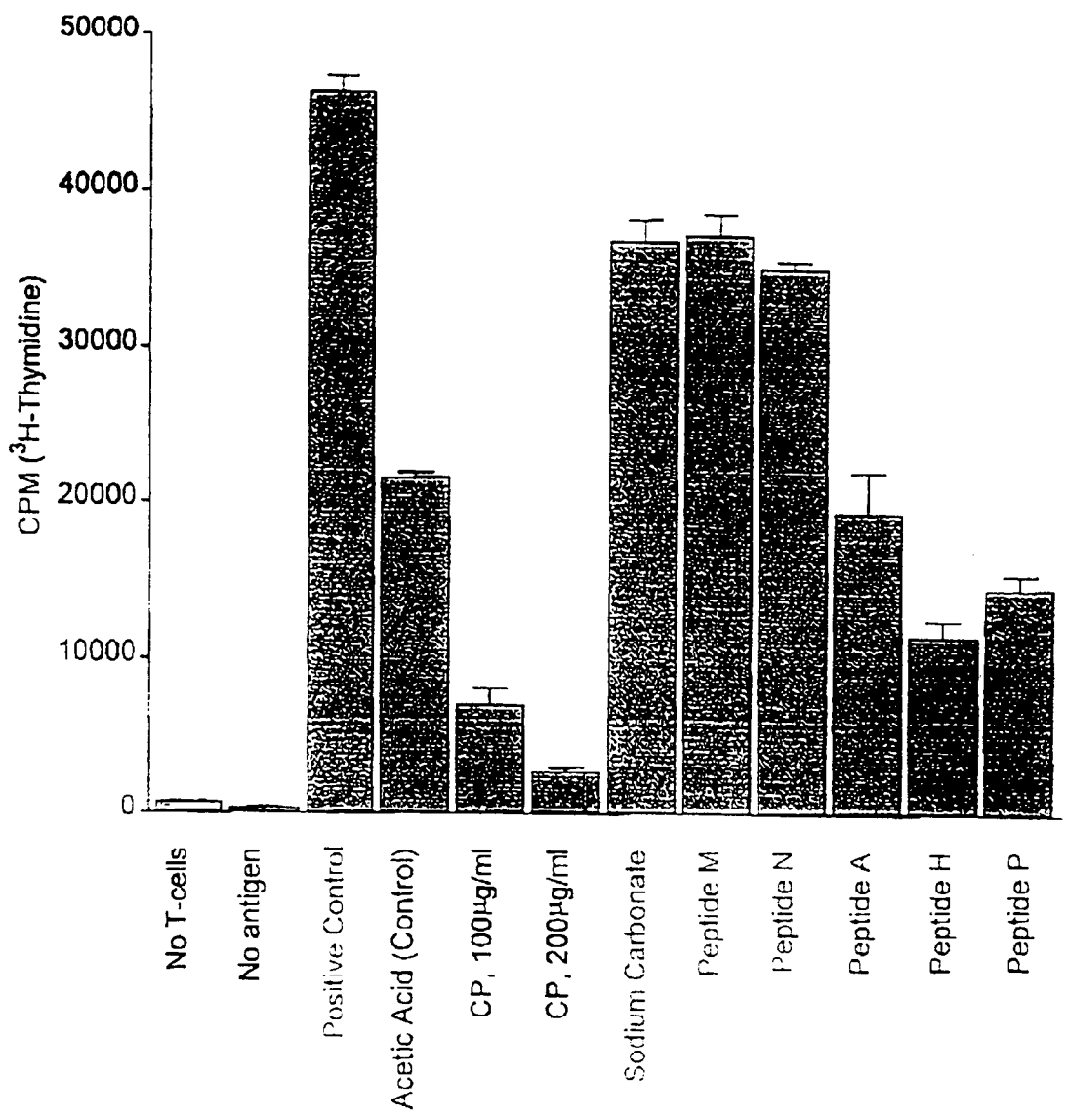

FIG. 5—Effect of peptides on an MTB-specific T-cell line. Shown are means and standard errors (n=4). Peptide final concentrations were 100 µM except where stated. Core peptide (CP) at 0.1 mg/ml is 87 µM.

Figure 6:
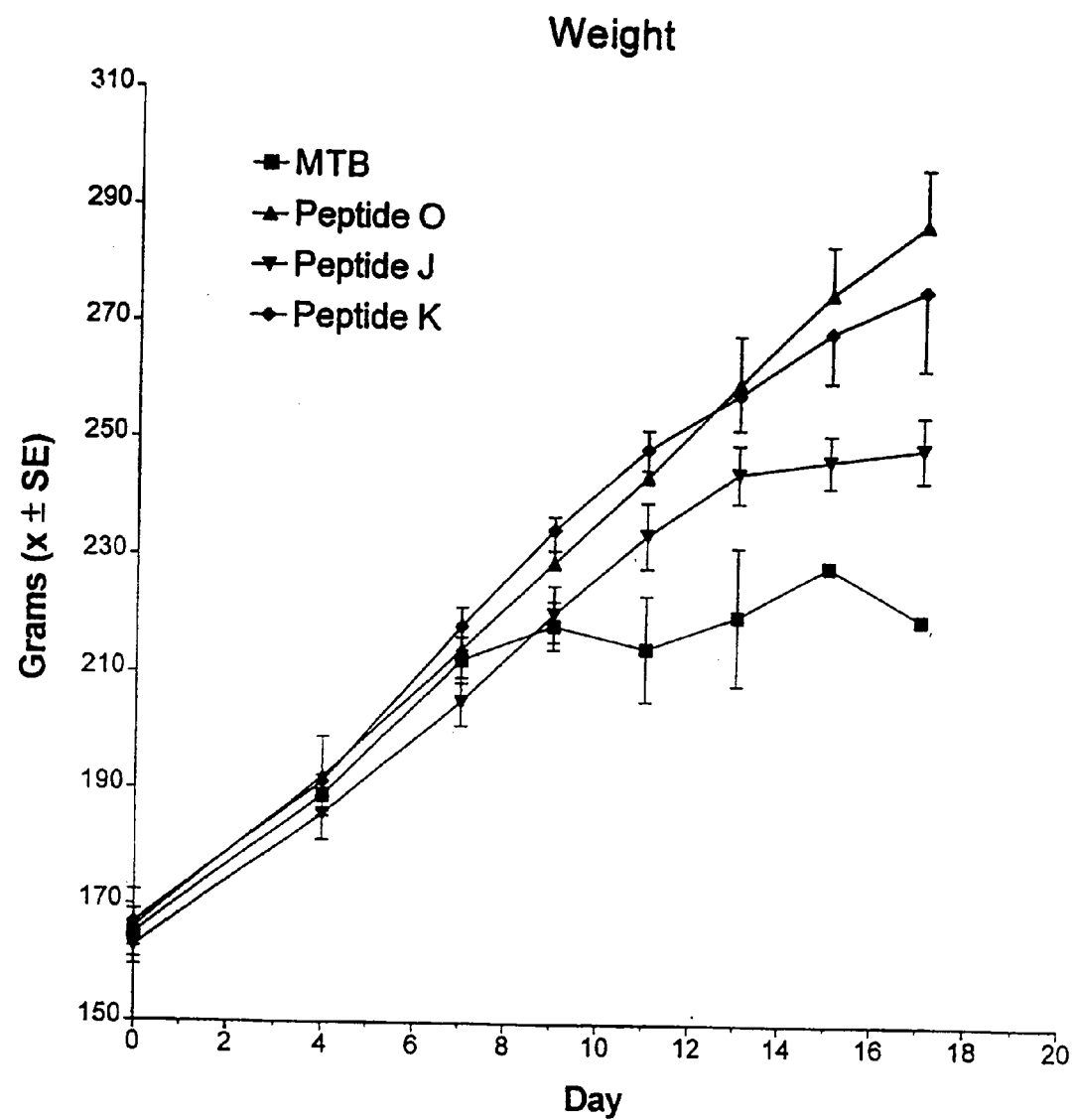

FIG. 6—Weight of treated and untreated rats. Shown are the means and standard errors of five rats in each group.

Figure 7A:
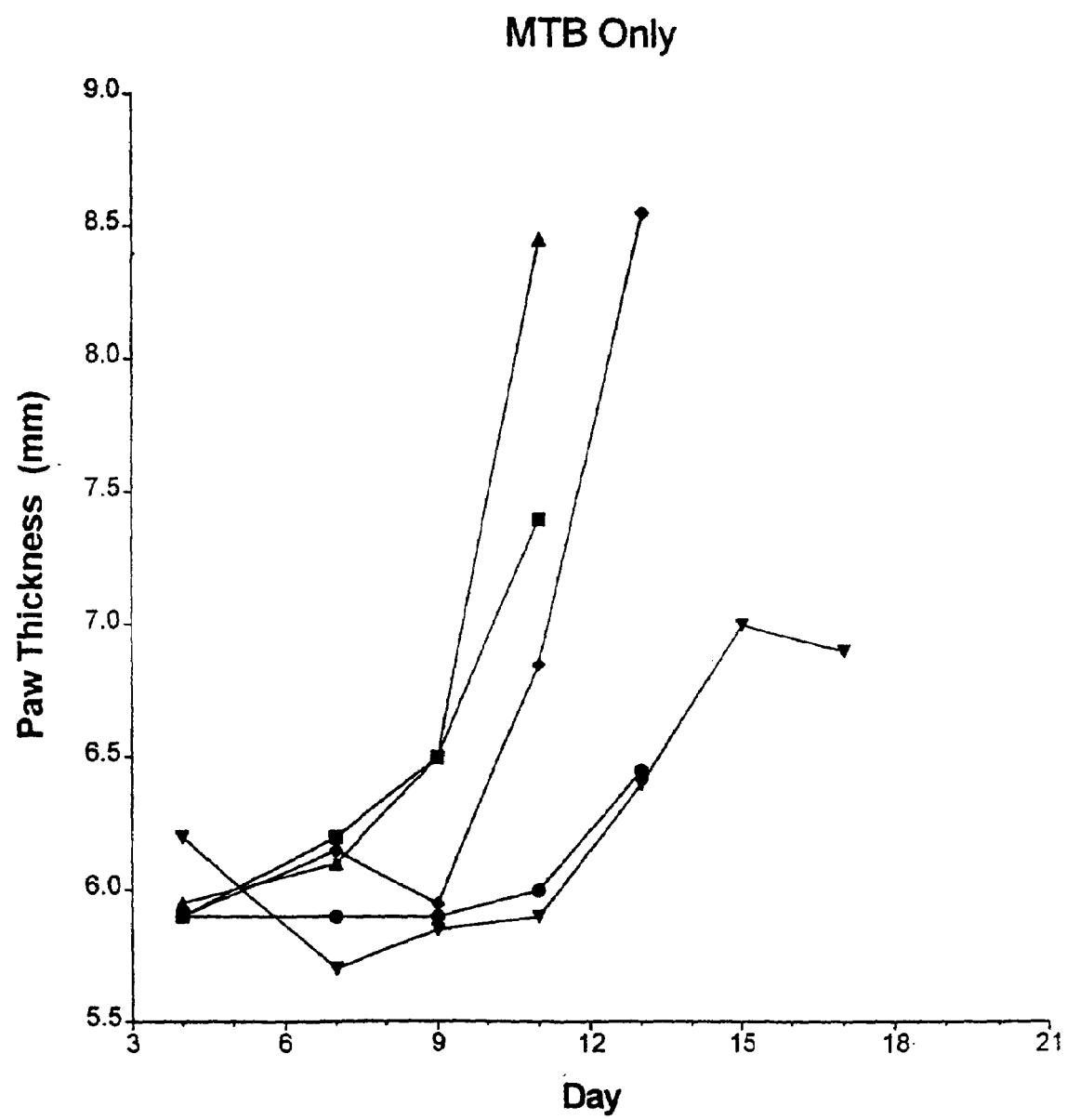

FIG. 7(a)—Paw thickness in untreated rats. Each point represents the mean of both hind paws of each rat.

Figure 7B:
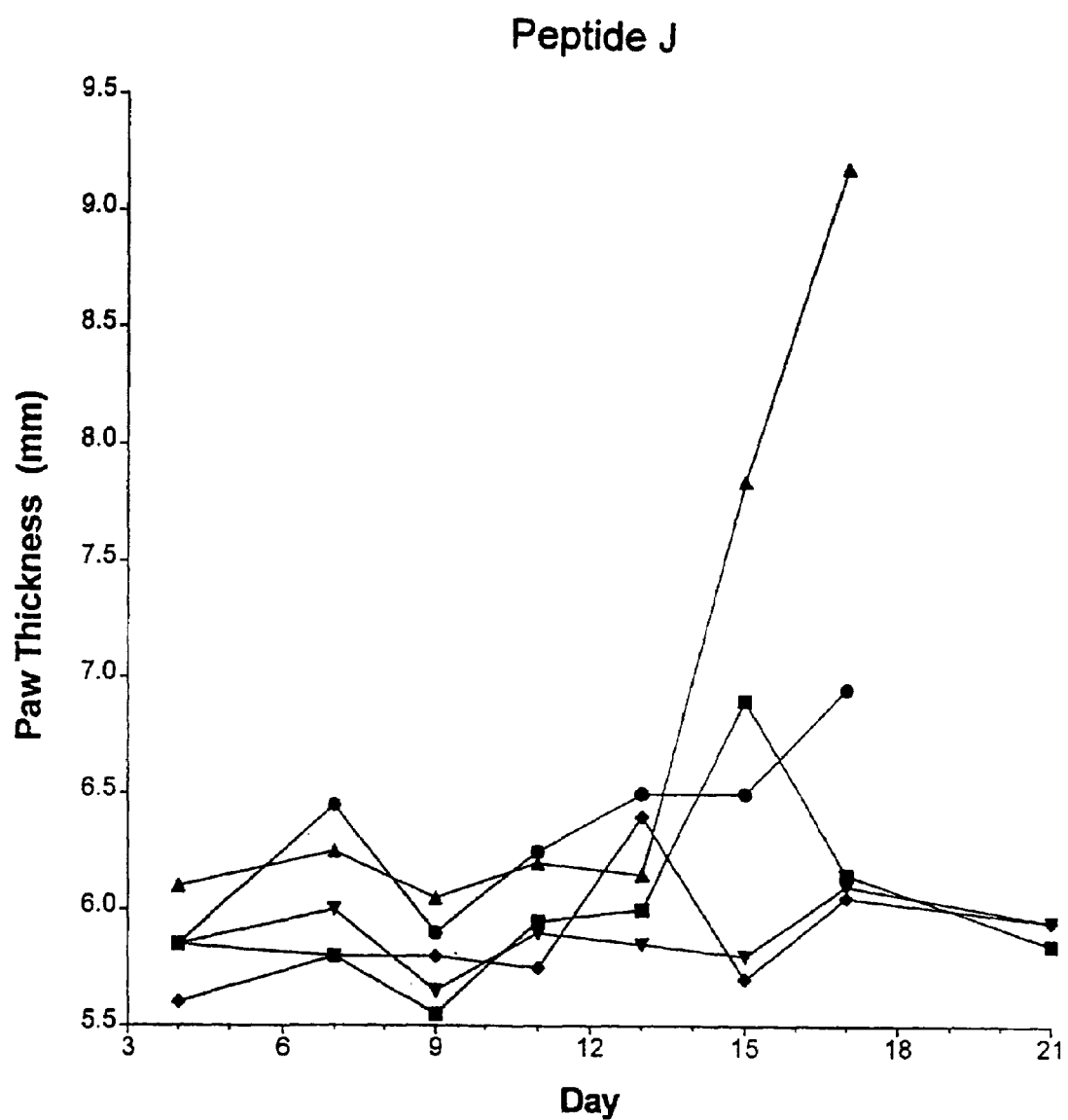

FIG. 7(b)—Paw thickness in peptide-J treated rats. Each point represents the mean of both hind paws of each rat.

Figure 7C:
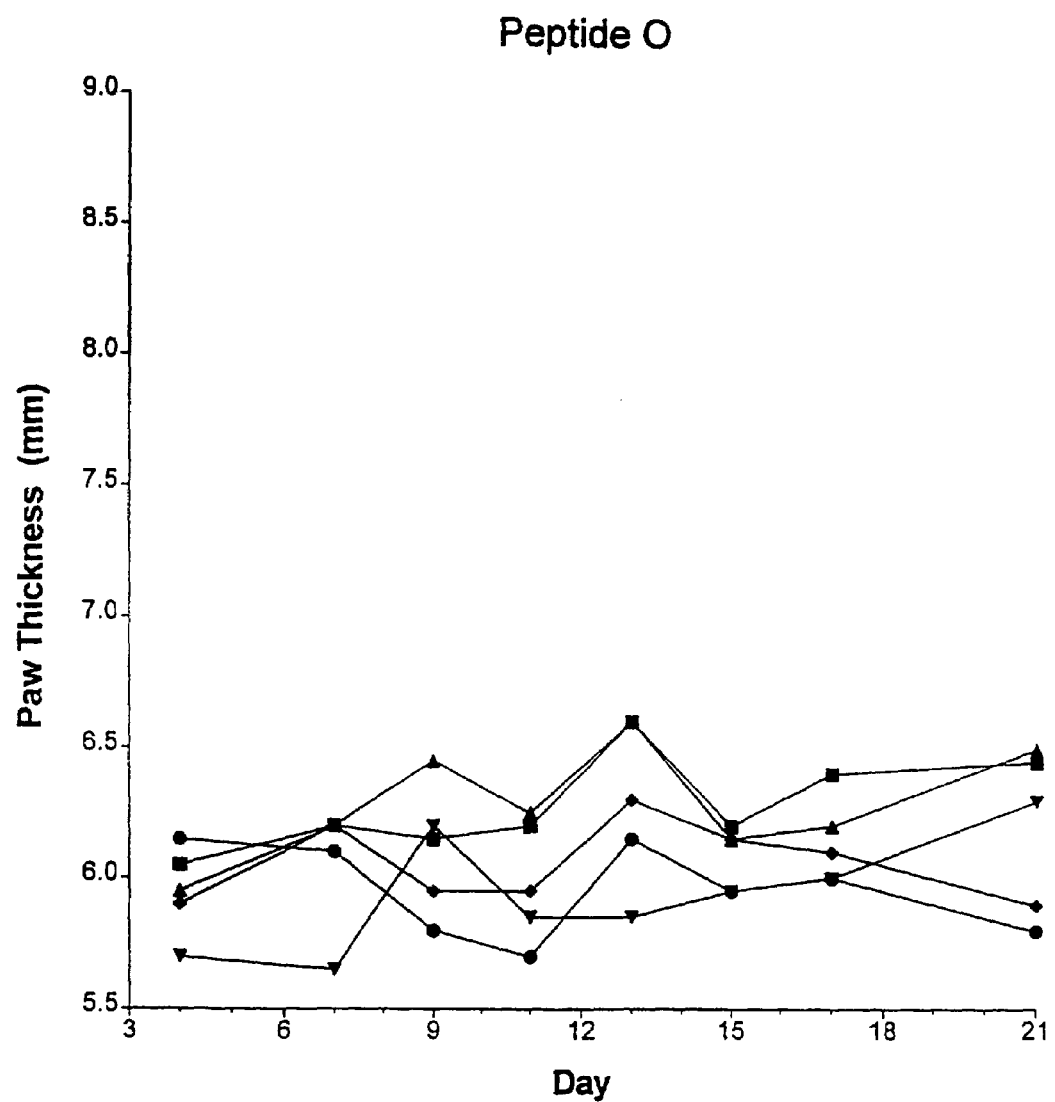

FIG. 7(c)—Paw thickness in peptide-O treated rats. Each point represents the mean of both hind paws of each rat.

Figure 7D:
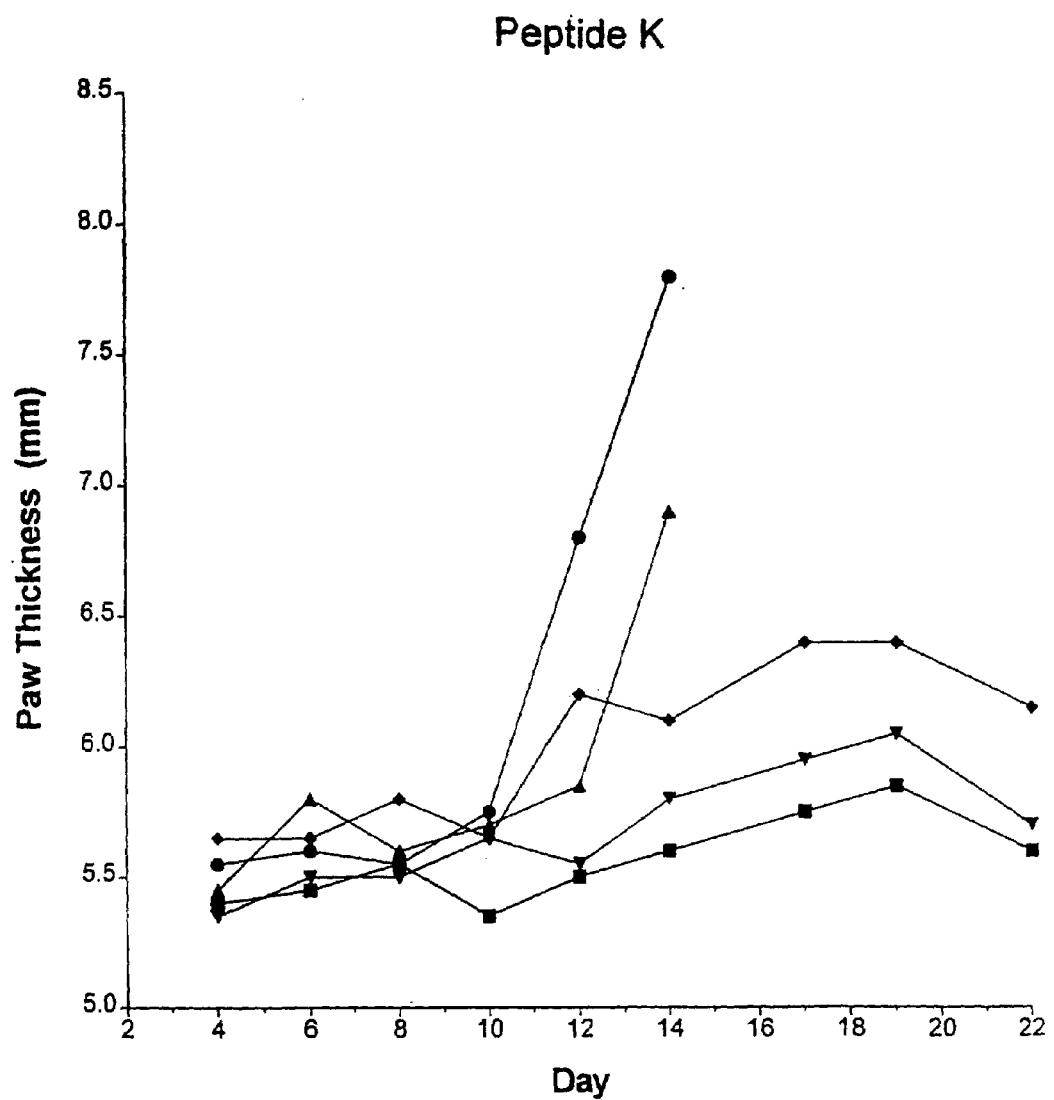

FIG. 7(d)—Paw thickness in peptide-K treated rats. Each point represents the mean of both hind paws of each rat.

Figure 8:
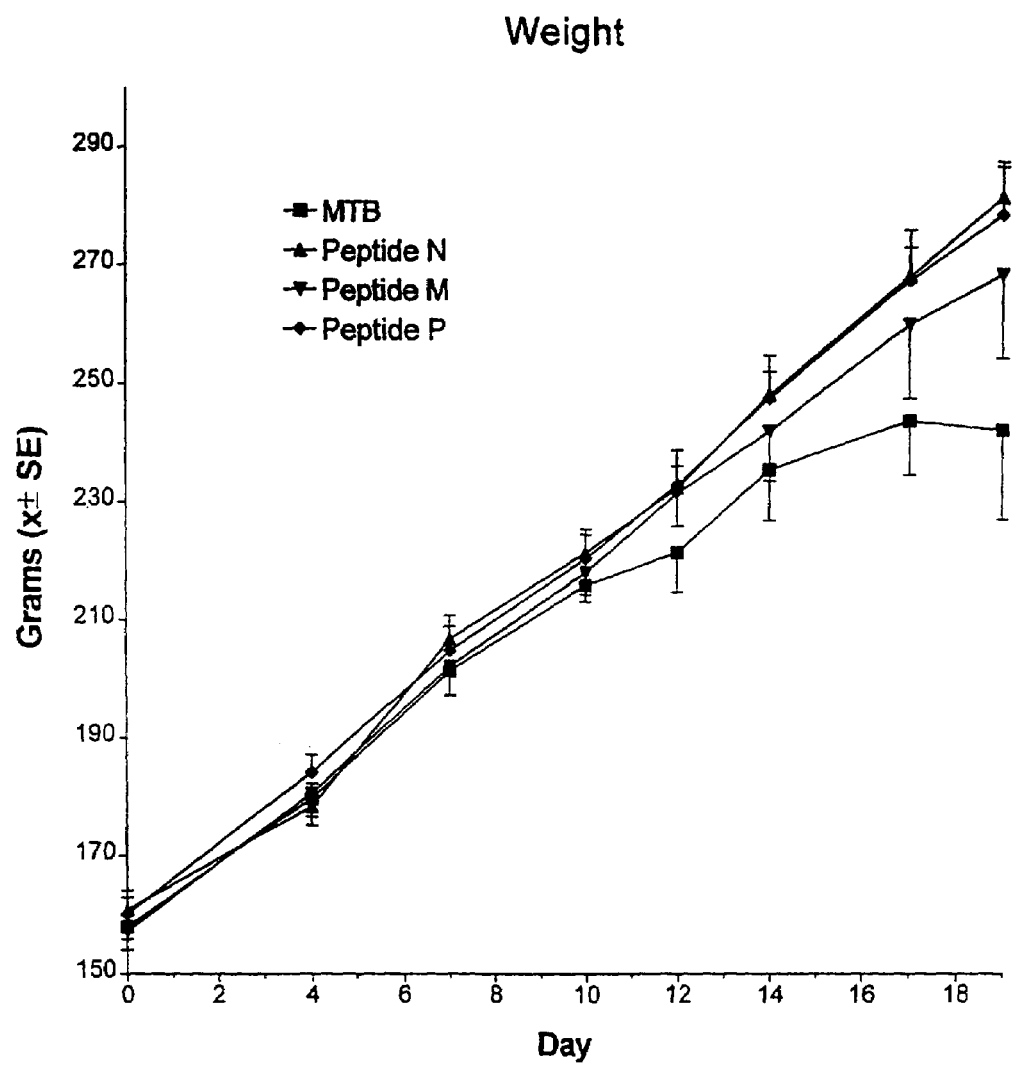

FIG. 8—Weight of untreated (MTB only) and treated (peptides N,M,P) rats. Shown are the means and standard errors of five rates in each group.

Figure 9A:
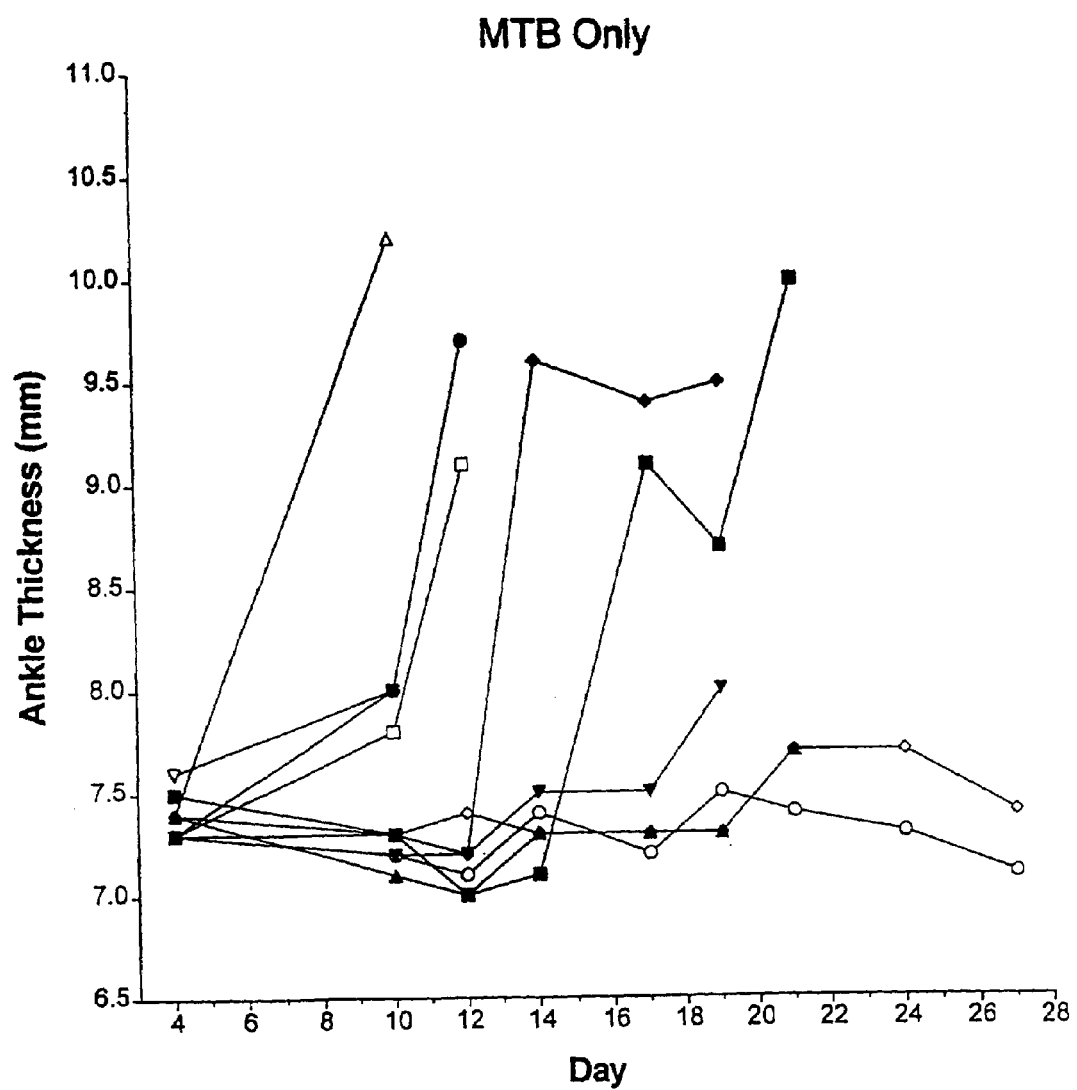

FIG. 9(a)—Ankle thickness of untreated rats. Each point represents the thickness of individual ankle joints.

Figure 9B:
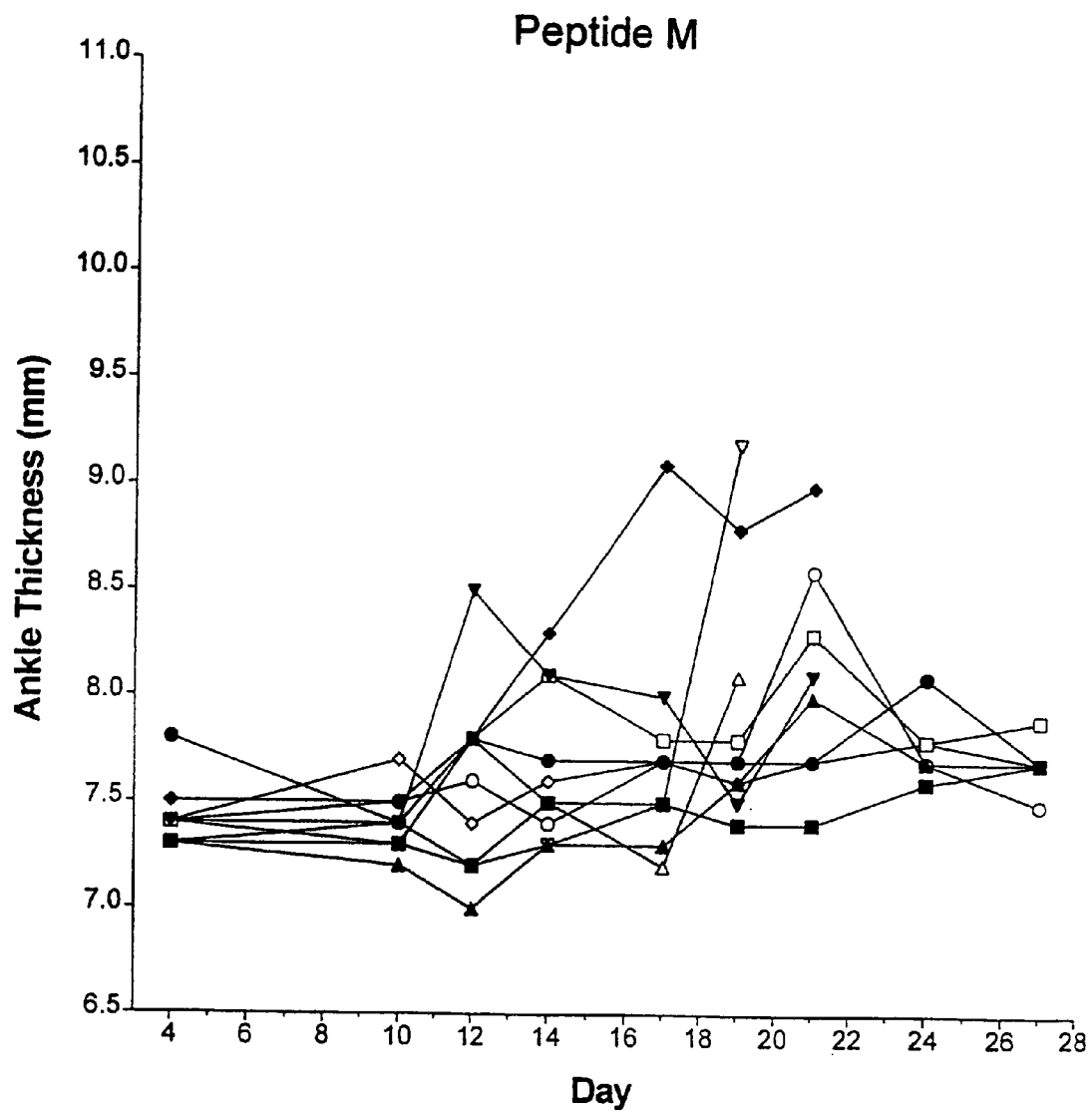

FIG. 9(b)—Ankle thickness of peptide-M treated rats. Each point represents the thickness of individual ankle joints.

Figure 9C:
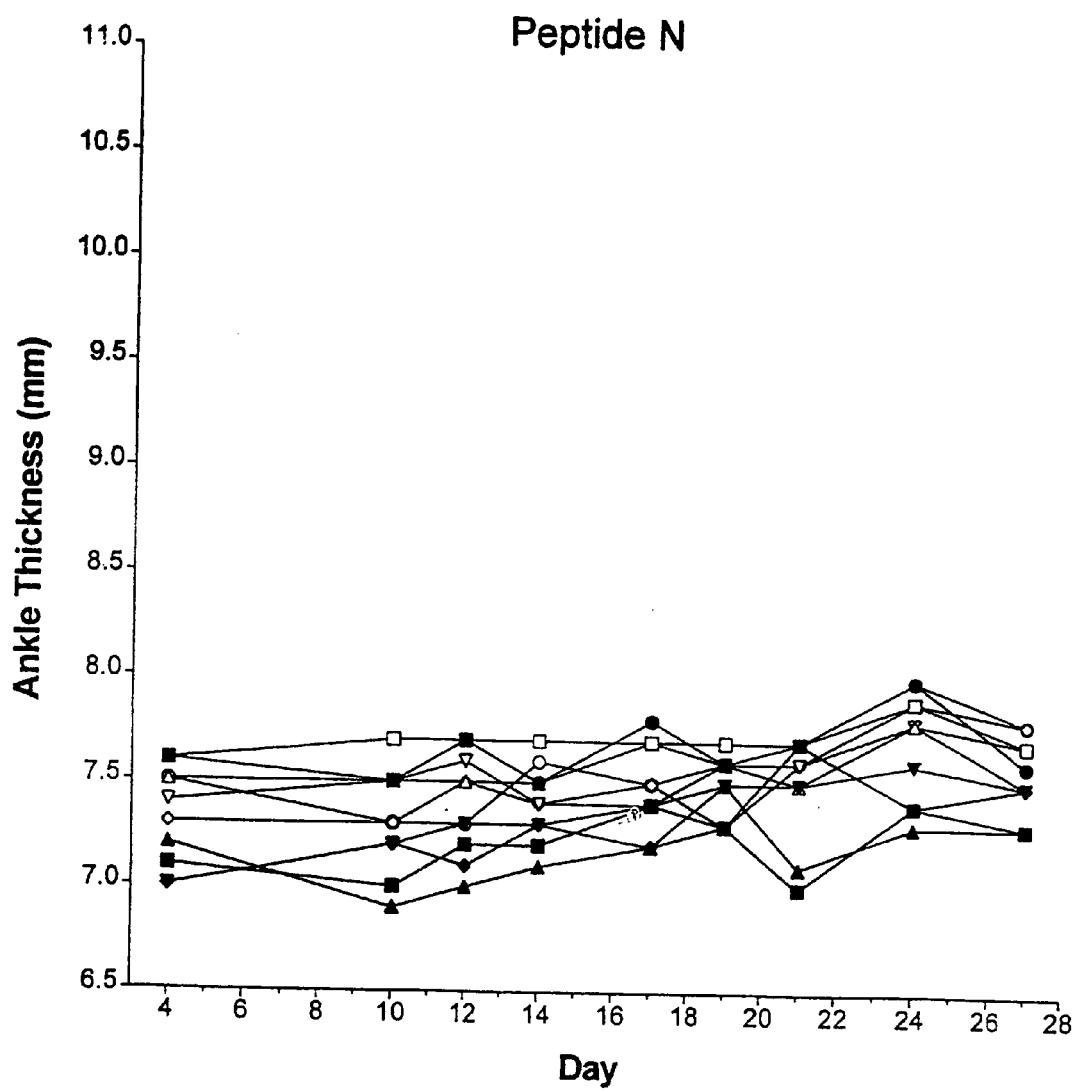

FIG. 9(c)—Ankle thickness of peptide-N treated rats. Each point represents the thickness of individual ankle joints.

Figure 9D:
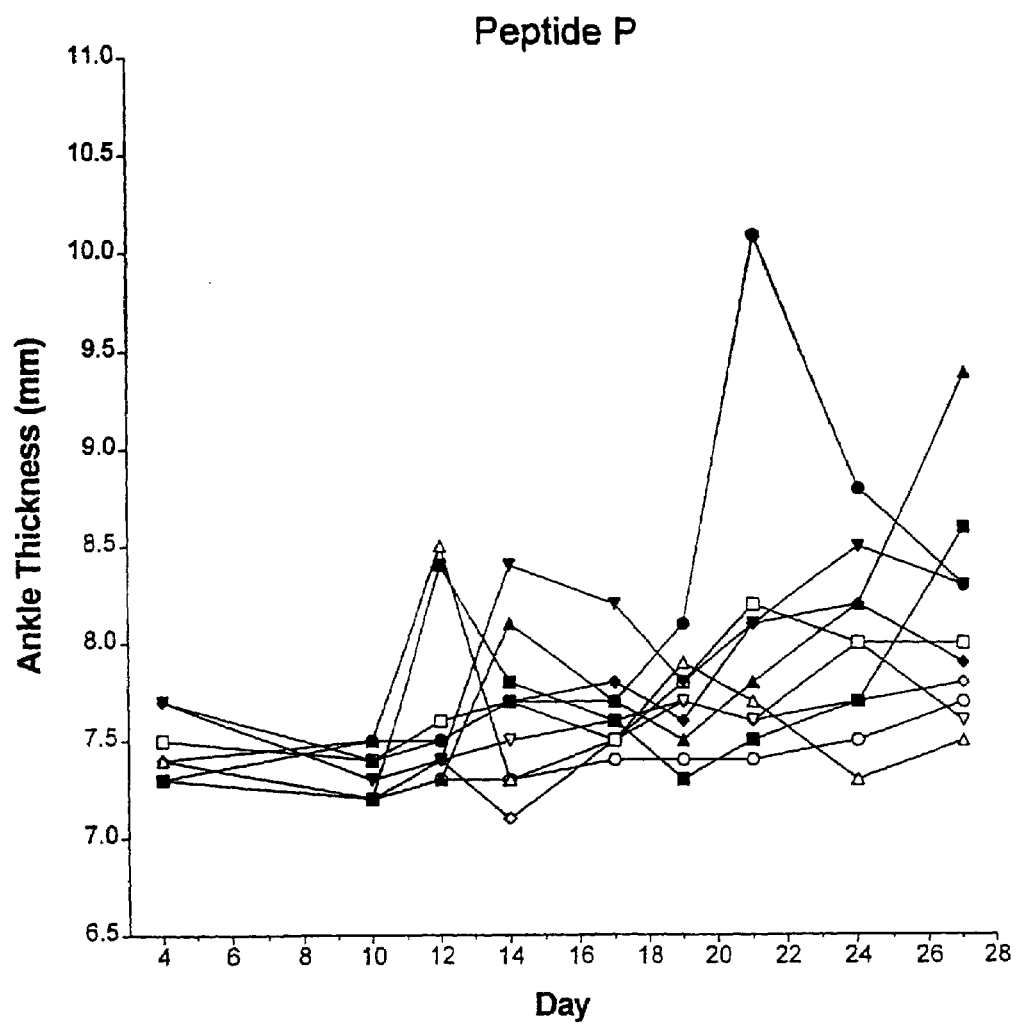

FIG. 9(d)—Ankle thickness of peptide-P treated rats. Each point represents the thickness of individual ankle joints.

Figure 10:
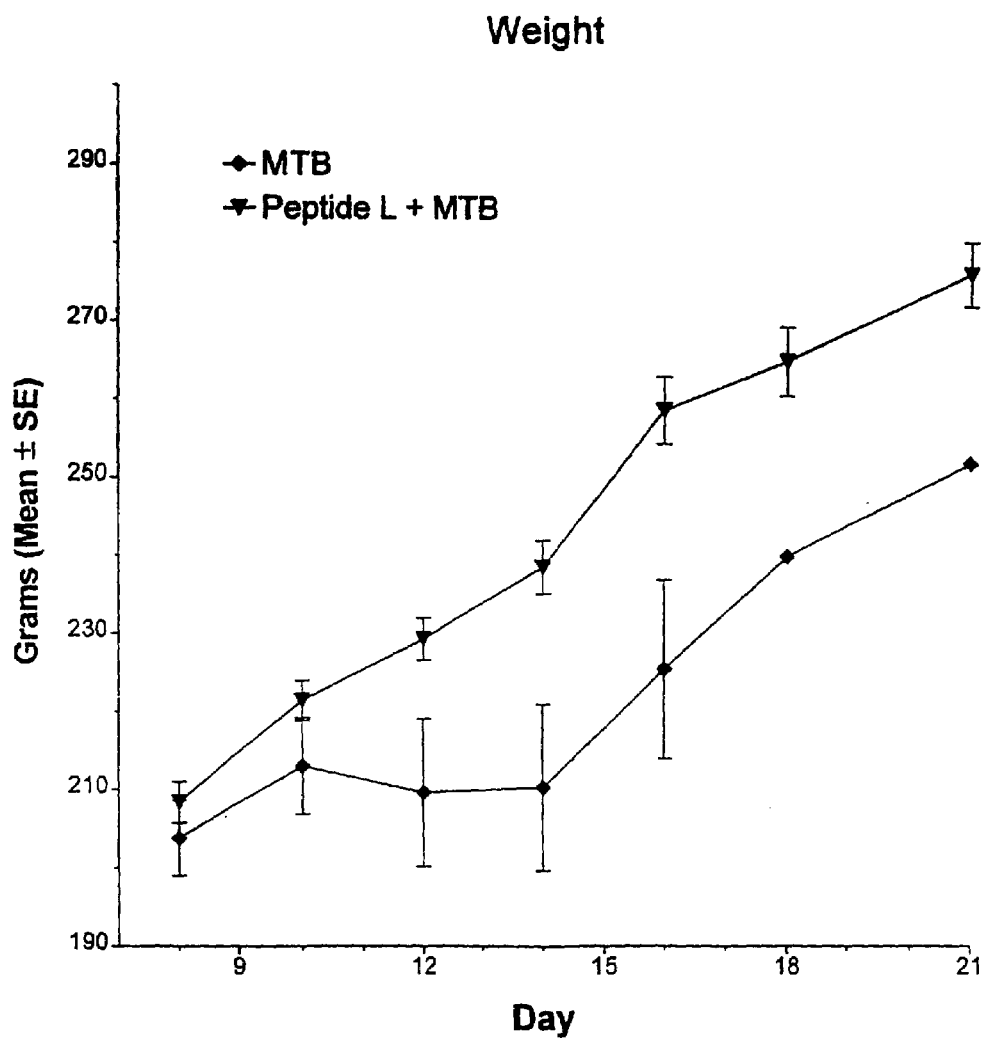

FIG. 10—Weight of peptide L-treated and untreated rats. Shown are the mean and standard errors of five rats in each group.

Figure 11A:
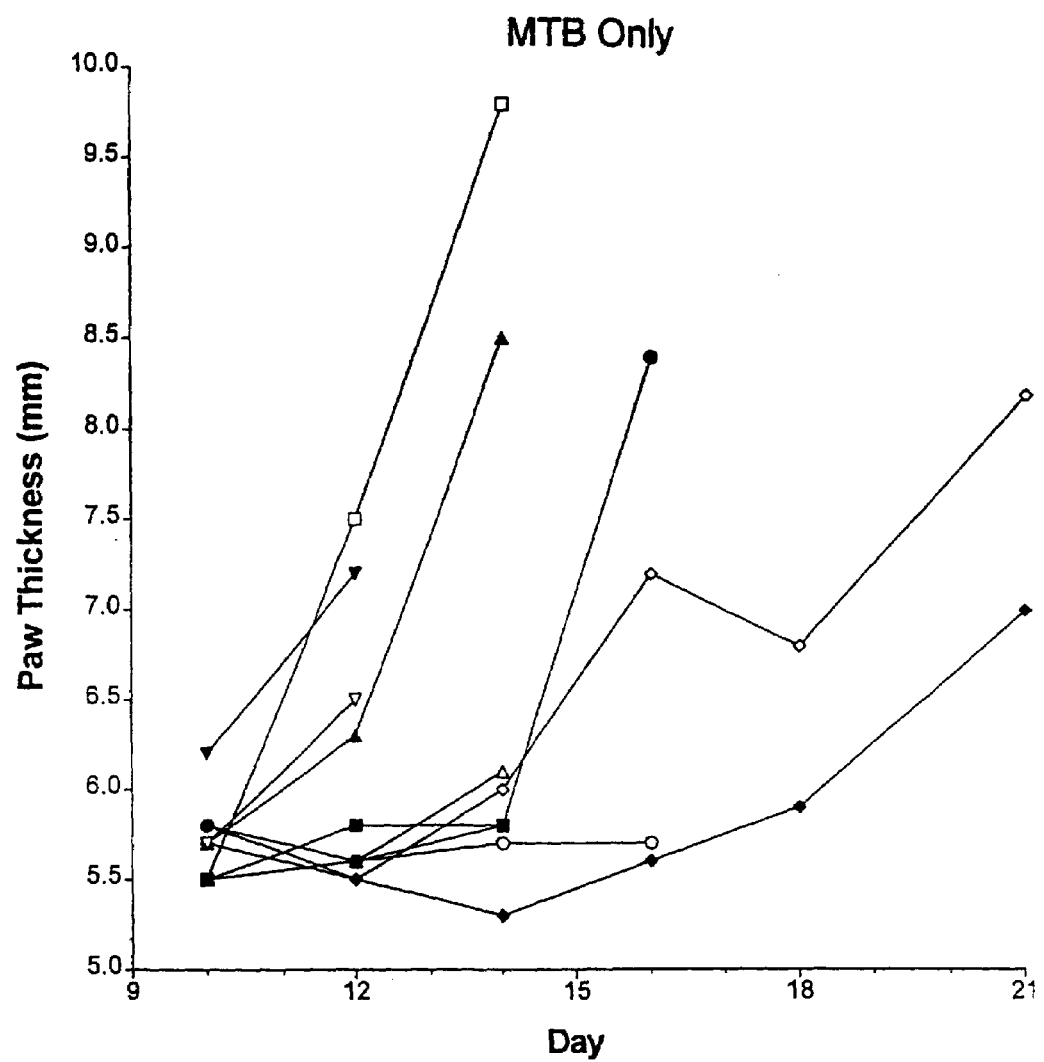

FIG. 11(a)—Paw thickness in untreated rats. Each point represents the thickness of an individual hind paw.

Figure 11B:
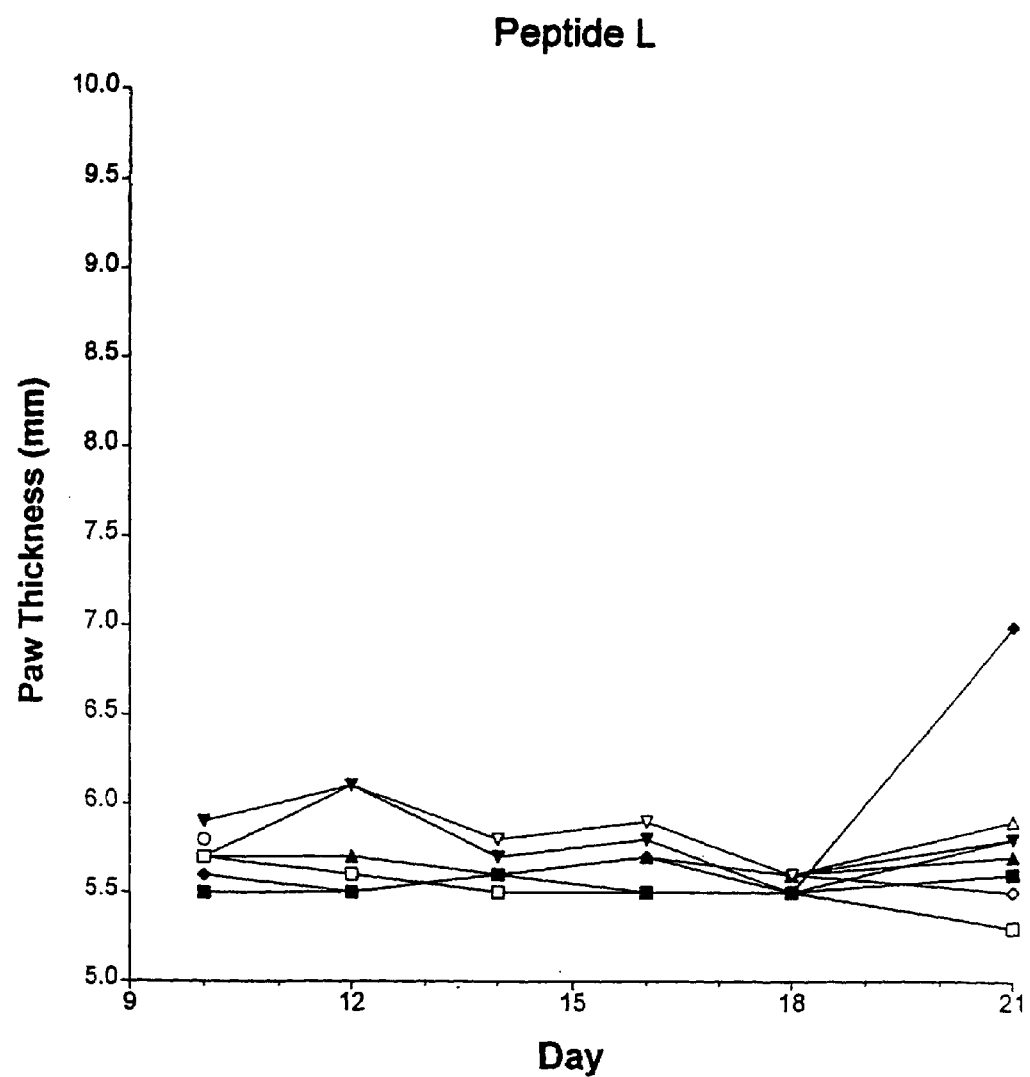

FIG. 11(b)—Paw thickness in peptide-L treated rats. Each point represents the thickness of individual hind paws.

Figure 11C:
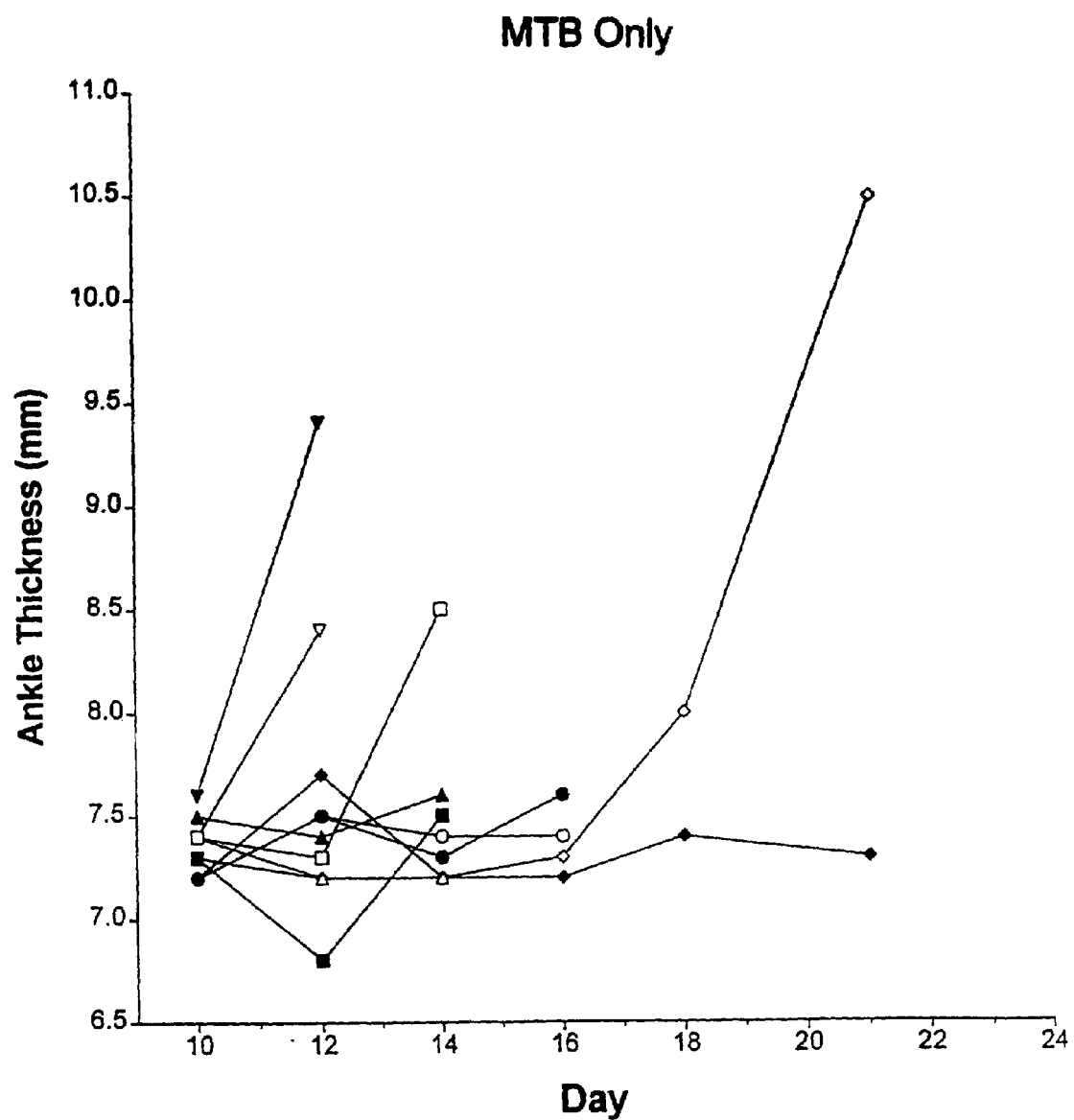

FIG. 11(c)—Ankle thickness of untreated rats. Each point represents the thickness of individual ankle joints.

Figure 11D:
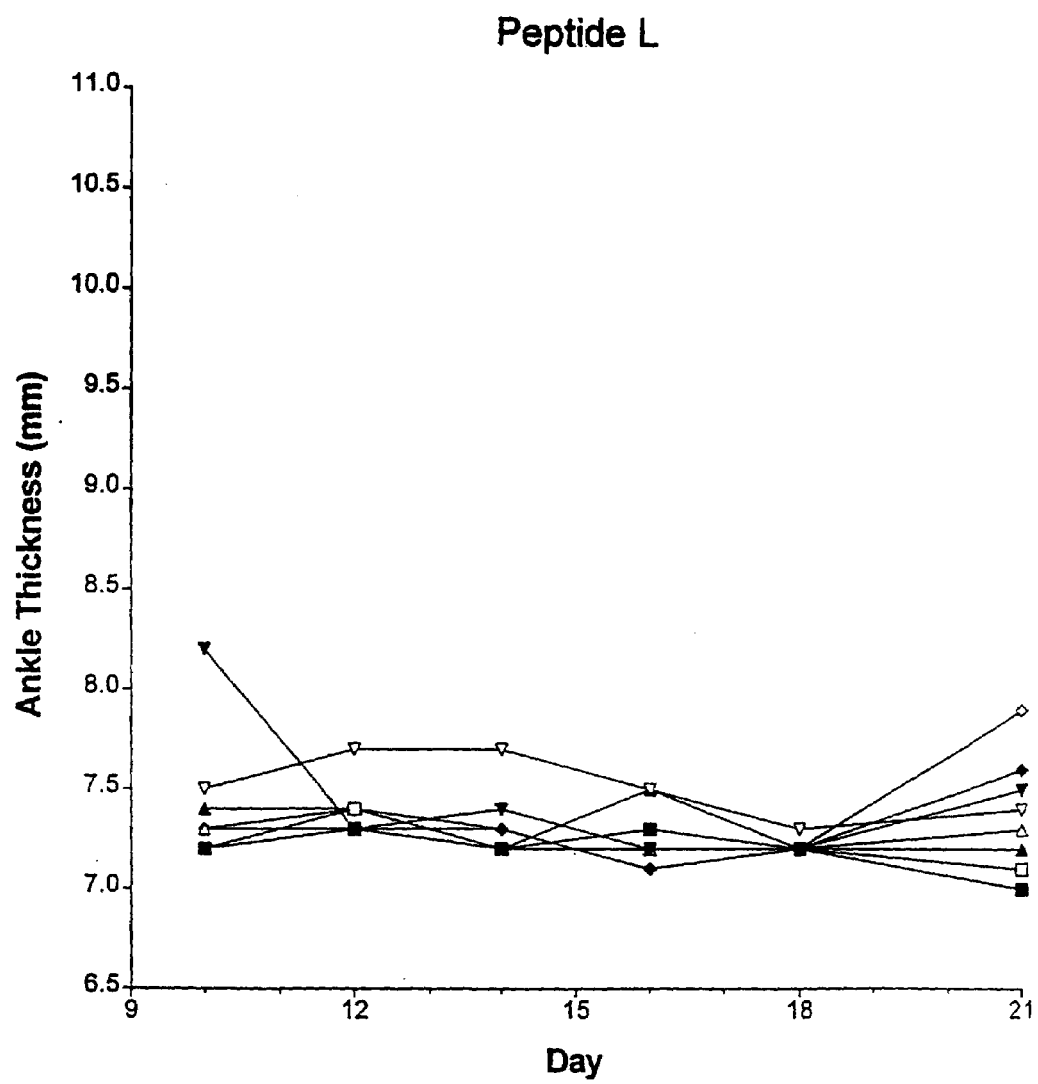

FIG. 11(d)—Ankle thickness of peptide-L treated rats. Each point represents the thickness of individual ankle joints.

EXAMPLES

Experimental Methods

Peptide synthesis. Peptides were synthesised by solid phase synthesis using FMOC chemistry in the manual mode. Unprotected peptides were purchased from Auspep (Melbourne, Australia) with greater than 75% purity as assessed by HPLC. An example of an enclosed specification sheet is attached in the Appendix. The final concentration of peptide dissolved in 0.1% acetic acid used in cell culture ranged from 10 µM–200 µM. For in-vivo studies, peptides were dissolved/suspended in squalane oil (2-,6-,10-, 15-,19-,23-hexamethyltetracosane).

Cells. The following cell lines were used: 2B4.11, a murine T-cell hybridoma that expresses a complete antigen receptor on the cell surface and produces IL-2 following antigen recognition (cytochrome-c): an interleukin-2 dependent T-cell line (CTLL) for conventional biological IL-2 assays; and the B-cell hybridoma cell line LK 35.2 (LK, I-E$^k$ bearing) which acts as the antigen presenting cell. The hybridomas were grown in T-cell medium (RPMI-1640 media containing 10% foetal calf serum (FCS), gentamycin (80 µg/ml), glutamine (2 mM) and mercaptoethanol (0.002%)). The African green monkey kidney fibroblast cell line (COS) was grown in Dulbecco's modified Eagle's medium (DMEM) supplemented with 10% FCS.

Antigen presentation assay[36]. The mouse T-cell 2B4.11 hybridoma ($2\times10^4$) was cultured in microtitre wells with LK35.2 antigen presenting B cells ($2\times10^4$) and 50 µM pigeon cytochrome-c. After 16 hr 50 microliters of assay supernatant was removed and assayed for the presence of IL-2. Serial twofold dilutions of the supernatant in media were cultured with the IL-2 dependent T-cell line CTLL. After 16 hr the CTLL cells were pulsed with $^3$H-thymidine for 4 hr and IL-2 measurements (IU/ml) determined. Peptides examined included: CP, A, B, C, D, E, F, G. H, I, J, K, L, M. N, O, and P (Table 2). Peptide L was very insoluble and was not tested in vitro. The peptides were tested in the antigen presentation assay at final concentrations ranging from 10 µM to 200 µM.

Primed Lymph Node Cells (PLNC). Male Wistar rats were injected intradermally at the base of the tail with 1 mg of heat-killed *Mycobacterium tuberculosis* (MTB) suspended in 0.2 ml of squalane. When acute arthritis was well developed, after 10 to 16 days, rats were killed and the swollen popliteal lymph nodes were removed and a single cell suspension made by pressing the tissue through a fine sieve under aseptic conditions. Cells were washed in complete medium, resuspended and counted. Approximately $3.5 \times 10^8$ viable cells were obtained from two rats. The medium used was RPMI 1640 supplemented with 25 mM Hepes, penicillin (100 µg/ml), streptomycin (80 µg/ml), $2.5 \times 10^{-5}$ M 2-mercaptoethanol and 2% pooled normal rat serum. The cells were pipetted into the wells of flat-bottom, 96 well microtitre plates at $2 \times 10^5$/well and a suspension of MTB was added to a final concentration of 100 µg/ml. Peptides were delivered to the wells in 20 µl volume giving final concentrations of 100 µg/ml peptides (or 100 µM) and 0.01% acetic acid, and a total of 200 µl per well. The plates were incubated at 37° C. in a humidified incubator at 5% $CO_2$ for 3 days and then were pulsed with 1 µCi per well of 3H-thymidine in 25 ml of medium. After a further overnight incubation, the cultures were harvested using an automated cell harvester, and counted in a β-scintillation spectrometer.

T-Cell Lines. The method used was by Sedgwick et al (1989)[37]. PLNCs from MTB-immunised rats were cultured in 75 cm² culture flasks at $5 \times 10^6$ per ml in a total of 50 ml containing 100 µg/ml MTB. After three days the cells were spun down and resuspended in 2 ml medium in a 15 ml centrifuge tube and were underlayered with 3 ml of Ficoll diatrizoate (9.9% Ficoll 400; 9.6% sodium diatrizoate), and centrifuged at 800 g for 20 minutes. The T-cell blasts were recovered from the interface, washed twice and resuspended at $2 \times 10^5$ per ml in medium supplemented with 10% FCS and 15% con A-stimulated spleen cell supernatant, as a source of IL-2. After four days culture in the rest phase, $2 \times 10^5$ T-cells per ml were restimulated with antigen and $10^7$ syngeneic rat thymocytes per ml to act as antigen presenting cells. The latter had been inactivated by incubation with 25 µg/ml mitomycin C for 20 minutes at 37° C. and carefully washed three times. Cultures were in 75 cm² flasks containing 50 ml and the antigen, MTB, was added at 100 µg/ml. Flasks were stood up vertically and cultured for 3 days. Again T-cell blasts were recovered by separation on Ficoll/diatrizoate, and the cycle was repeated. After 2–4 cycles, the cells were set in 96-well plates at $10^4$ T-cells/well and $10^6$ mitomycin-C-inactivated thymocytes, in 200 ml medium containing 100 µg/ml MTB and 2% rat serum. Additions of 20 µl were made to the wells containing peptides in 0.1% acetic acid. Cultures were incubated for three days, then 3H-thymidine (1 µCi in 25 ml medium) was added and the incubation continued overnight after which it was harvested and counted in the β-counter. Results are shown as count2 per minute (cpm) tritiated thymidine incorporation. The peptides tested in these assays for the ability to inhibit antigen-stimulated T-lymphocyte proliferation are shown in Table 2.

TABLE 2

Synthetic peptides and their sequence.

| Peptide | Sequence | MWt | No. AAs | Chain of Origin/Domain | |
|---|---|---|---|---|---|
| CP | G L R I L L L K V | 1024 | 9 | TCR-α transmembrane | (SEQ ID NO. 21) |
| A | M G L R I L L L | 928 | 8 | TCR-α transmembrane | (SEQ ID NO. 22) |
| B | I L L L K V A G | 826 | 8 | TCR-α transmembrane | (SEQ ID NO. 7) |
| C | L G I L L L G V | 797 | 8 | TCR-α transmembrane | (SEQ ID NO. 23) |
| D | L K I L L L R V | 967 | 8 | TCR-α transmembrane | (SEQ ID NO. 24) |
| E | L D I L L L E V | 927 | 8 | TCR-α transmembrane | (SEQ ID NO. 25) |
| F | L R I L L L I K V | 1080 | 9 | TCR-α transmembrane | (SEQ ID NO. 26) |
| G | L R L L L K V | 854 | 7 | TCR-α transmembrane | (SEQ ID NO. 8) |
| H | L R I L L L G V | 896 | 8 | TCR-α transmembrane | (SEQ ID NO. 9) |
| I | L G I L L L K V | 868 | 8 | TCR-α transmembrane | (SEQ ID NO. 17) |
| J | Y G R A D G G I T S | 1042 | 10 | TCR-α extracellular (SS) | (SEQ ID NO. 18) |
| K | S S D V P C D A T L T | 1108 | 11 | TCR-β extracellular (SS) | (SEQ ID NO. 14) |
| L | I V I V D I C I T | 988 | 9 | CD3-ε transmembrane | (SEQ ID NO. 13) |
| M | I I V T D V I A T L | 1057 | 10 | CD3-δ transmembrane | (SEQ ID NO. 15) |
| N | F L F A E I V S I | 1038 | 9 | CD3-γ transmembrane | (SEQ ID NO. 16) |
| O | A G F N L L M T | 866 | 8 | TCR-α intracellular (1) | (SEQ ID NO. 12) |
| P | L L M T L R L W S S | 1220 | 10 | TCR-α intracellular (2) | |

AA, amino acids: MWt. molecular weight.

Adjuvant-induced arthritis in rats. Arthritis in rats was induced by a single intradermal injection of heat killed MTB in 200 µl squalane (adjuvant) at the base of the tail. Peptides (35 mg) were suspended in one milliliter squalane containing 5 mg of MTB. That is, there was 1 mg MTB and 7 mg peptide in 0.2 ml of squalane injected intradermally. At regular intervals for up to 28 days, animals were weighed and their arthritic condition assessed by measurement of ankle thickness and rear paw thickness (with a micrometer) and recording the number of arthritic joints involved. Rats were housed in standard cages after the initial tail injection and allowed access to unlimited water and pellet food. Rats generally developed arthritis 12–14 days after the injection. Consistent with previous reports, not all rats given MTB/squalane developed arthritis. In our case the success rate was more than 80% of MTB injected control rats developing arthritis. On day 29, the animals were sacrificed.

Results (a) In-Vitro.

Effect of T-Cell Receptor Peptide and its Variants on Antigen-Stimulated Proliferation on Rat Primed Lymph Node Cells (PLNC) and T-Cell Lines Initial experiments which attempted to demonstrate an effect of peptide on T-cell function in vitro used an antigen presenting assay. The mouse T-hybridoma 2B4, specific for the protein cytochrome c, was presented with antigen by the LK cell line, and the IL-2 content in the supernatant was bioassayed by measuring the proliferation of the IL-2 dependent line, CTLL[5]. As hybridomas can be phenotypically unstable, primary T-cells would be a better model and lymph node cells from rats immunised with heat killed MB were used.

PLNC Experiment 1. The assay showed a strong inhibitory effect of core peptide on T-cell proliferation (FIG. 2), reducing counts to approximately 10% of the vehicle control. There was negligible proliferation in the absence of antigen, confirming that counts were reflecting T-cell response to antigen, i.e., genuine T-cell function. Interestingly, some of the modified peptides also had activity. Peptide H appeared to reduce T-cell proliferation.

PLNC Experiment 2. In this experiment, the background counts in wells with no antigen were very high, above 10000 cpm (FIG. 3). Even so, the vehicle control was much higher at 40000 cpm, so the results were still interpretable. The aims of this experiment were to use the more robust model of PLNC cultures to again test peptides alone and in combination. As different peptides would be hypothesised to work on the different parts of the T-cell receptor from which they were derived (Table 2), peptides from different chains used in combination might act synergistically. It can be seen from FIG. 3 that core peptide reduced antigen-stimulated T-cell proliferation, whether freshly dissolved or stored for more than three months at 4° C. Peptide P also showed activity. Peptides M and N did not reduce proliferation. Combinations of peptides M+CP, CP+P, CP+P+N and P+N+M resulted in reduced 3H-thymidine approximately equal to the average of their individual effects and no synergistic actions of combined peptides was noted.

T-Cell Line Experiment 1. The control, containing just the vehicle (20 µl 0.1% acetic acid) alone reduced the counts considerably compared with the untreated positive control, from over 50000 to approximately 30000 (FIG. 4). This was not the case in PLNC experiments where the vehicle alone had no effect. Core peptide at 100 µg/ml reduced counts further to approximately 18000 cpm, and 200 µg/ml core peptide further reduced counts to about 25% of the control level. Peptides H and P also diminished cell proliferation by 50% or more, compared to the vehicle control. In the absence of antigen, there was about a 4000 cpm background in this experiment.

T-Cell Line Experiment 2. As in the previous experiment, T-cell line cells were adversely affected by the vehicle alone, with counts reflecting proliferation, reduced to about half of the positive control value (FIG. 5) however non-specific stimulation of T-cells in the absence of antigen was negligable. Core peptide at a concentration of 100 µM reduced counts further to approximately 33% of its vehicle control and at 200 µM, 16% of the control. The buffer control for peptides M and N, which was 0.05M sodium carbonate, pH 9.6 (5 mM in the well), was not as detrimental to the assay as 0.1% acetic acid (1.75 mM in the well), resulting in a slight reduction in 3H-thymidine incorporation compared with the positive control (data not shown). However peptides M and N (100 µM) showed no effects on T-cell proliferation. Peptide H reduced counts to 66% of controls and peptide P had a marginal effect.

Discussion. It has been shown in these experiments that T-cell receptor peptides can inhibit T-cell proliferation in response to challenge with the specific antigen to which the cells had been primed. This was shown both for primary lymph node cultures, and for T-cell lines established in culture. The most profound result was in the first experiment by CP which reduced proliferation by go %. Peptides H also consistently reduced counts compared to the acetic acid vehicle control but not to the same extent. Peptide P was most inhibitory in FIG. 2 and also effective in FIGS. 3 and 4.

The solubility of the peptides was variable. At the concentration of the stock solutions, 1 mg/ml or 1 mM, most peptide solutions looked clear. Exceptions were peptides H, I, O, P, which were turbid or had undissolved particles. Therefore, the true concentration of peptides in solution in the culture wells would be less than those nominated in the case of these partially soluble peptides. Core peptide could be dissolved at 2 mg/ml, but was not completely soluble at 5 mg/ml. When 20 µl of these stock solutions were added to the wells, 0.2 mg/ml CP was more inhibitory than 0.1 mg/ml, however, 0.5 mg/ml was less effective, as the peptide precipitated upon addition to the well. The vehicle for the peptides, except M and N, was 0.1% acetic acid which gave 0.01%, i.e., 1.75 mM in the wells. The HEPES-buffered medium effectively buffered this acidity, but in addition to the acetate concentration, the medium was effectively reduced in concentration to 90%. This did not adversely affect the antigen-stimulated proliferation of primary lymph node cell cultures (data not shown), but has a marked effect on cultures of T-cell lines, reducing tritiated thymidine incorporation by 50%. In these experiments, effects of peptides could still be determined by comparison with the vehicle control. The 0.05M sodium carbonate buffer, used to dissolve peptides M and N, was not as detrimental to line T-cells as acetic acid. Peptide L was not tested as it was extremely insoluble. Interestingly, the only peptide that reduced T-cell proliferation which was not a CP derivative was peptide P, and it also originated from the TCR alpha chain. Peptides K, M and N, from the beta, delta and gamma chains, were soluble in their respective buffers.

In summary the core peptide, representing the transmembrane domain of TCR alpha, and including the two charged amino acids, was effective at inhibiting antigen-stimulated T-cell proliferation of both PLNCs and line T-cells, in each experiment. The degree of inhibition varied between 50% and 9096 in the different experiments. A peptide from the intracellular domain of the TCR-α chain, peptide P, also showed activity, but the peptides from the other TCR chains did not overtly inhibit proliferation of T-cells in these assays.

(B) In-Vivo.

Effects of T-Cell Receptor Peptides in Adjuvant Induced Arthritis in Rats.

Peptides were examined in groups based on availability. As such the results are reported in four sections.

(i) Examination of Peptide A, B, H and I.

Methods. The first experiment consisted of 12 rats weighing approximately 190–210 grams that were purchased from the Perth Animal Resource Centre (ARC) and maintained in the Gore Hill Animal House facility. Used were core peptide (30 mg) suspended in adjuvant (0.6 ml squalane containing 7 mg MTB), core peptide Tris-monopalmitate (15 mg) suspended in 0.6 ml adjuvant, core peptide Tris-tripalmitate 20 mg/0.6 ml of adjuvant. PCT/AU96/00018[5] describes a method of lipid peptide conjugation.

Rats were divided into four groups, each group containing three rats. First group received adjuvant only (positive control), second group adjuvant with core peptide, third group core peptide.Tris. monopalmitate suspended in adjuvant, and last group core peptide.Tris. tripalmitate in adjuvant. Rats were injected with the above compounds in a 0.1 ml volume at the base of the tail. Baseline measurements of rat weight, paw width, and tail diameter were made on Day 0, and subsequently on day 4, 7, 9, 14, 16, 18, 21, 25 and 28. Arthritis was graded and animals sacrificed if there was marked swelling, redness and obvious discomfort. Not all rats given MTB developed arthritis. In general more than 80% of control rats developed arthritis. Results. After 18 days all the control animals given adjuvant only had developed arthritis and had to be sacrificed. Two of the three core peptide treated animals (2/3) had no evidence of arthritis. Similarly, two of the three animals given core peptide.Tris-.tripalmitate had no evidence of arthritis. Animals given core peptide.Tris.monopalmitate and adjuvant all developed arthritis. However, the onset and development of arthritis in this latter group was prolonged by 3–4 days and the clinical severity was much reduced (number of joints, paw swelling, loss of weight) compared to controls.

Experiments using adjuvant induced arthritis in rats showed that the peptide and its lipid conjugate had a protective effect on the induction of arthritis in this animal model. Results of repeat and subsequent experiments using a number of different peptides (7 mg/rat) and drugs are summarised in TABLE 3.

TABLE 3

Effects of different peptides on adjuvant induced arthritis in rats.

| PEPTIDE | INDUCTION OF ARTHRITIS | | EFFECT |
|---|---|---|---|
| | MTB ALONE | WITH PEPTIDE | |
| CORE | 3/3 (100%) | 1/3 (33%) | Protective |
| | 3/5 (60%) | 1/5 (20%) | Protective |
| A | 5/5 (100%) | 1/4 (25%) | Protective |
| C | 2/4 (50%) | 2/4 (50%) | No effect |
| B | 4/5 (80%) | 1/4 (25%) | Protective |
| E | 4/5 (80%) | 4/5 (80%) | No effect |
| H | 5/5 (100%) | 3/5 (60%) | Protective |
| I | 5/5 (100%) | 2/5 (40%) | Protective |
| CS* | 5/5 (100%) | 1/5 (20%) | Protective |
| DXM* | 5/5 (100%) | 4/4 (100%) | No effect+ |

CS*, cyclosporin, 50 mg/kg; DXM, dexamethasone (2 mg/kg).
+, animals developed arthritis but the onset of arthritis was delayed by 3–4 days.

The results of the above experiments indicated that core peptide had an effect on inflammation both to delay its onset, decrease severity, and prevent onset of disease. These effects were similar to those obtained with the co-administration of cyclosporin and adjuvant. Cyclosporin is a well known and widely used immunosuppressive agent. There was no indiscriminate effect of peptide action. Best results were noted with core peptide and peptide B. In contrast there was no effect noted with peptide C or E having either no or negative charge group amino acids respectively. Extending the amino acids downstream towards the carboxy terminus had no negative effect. This observation confirms that carboxy modification can be performed without loss of biological activity. Therefore these peptides can be used as carrier peptides for the delivery of other chemical moieties.

(ii) Examination of Peptide J, K, O.

Methods. The weight of the Wistar rats averaged 165 grams on day of injection (day 0). Each rat was injected intradermally, at the base of the tail, using a 21 gauge needle, with 1 mg MTB in 200 µl squalane, with or without 7 mg of one of the test peptides suspended in this volume. A glass syringe was used.

Results. Early symptoms were observed as soon as day 7 in two of the control (MTB only) rats, and these were killed because of severe arthritis on Day 11. Two more controls were killed on day 13, and the fifth, on day 17. All five of the untreated control rats developed acute arthritis.

(1) Weight. FIG. 6 summarises the average weight of five rats in each group. From this figure it can be inferred that controls developed more severe disease whilst peptide treated rats developed less active disease. Of the peptide treated groups peptide O fared best whilst peptide K and J were protective.

(2) Paw thickness. Joint inflammation assessed as paw thickness in treated and untreated rats is shown in FIGS. 7(a–d). In addition to paw swelling, ankle swelling and individual joint counts were performed on each rat. The results reflect a similar trend noted in paw thickness. The above experiment was repeated exactly with similar results.

Discussion. Peptide J and K sequences are derived from the extracellular domain of TCR-α and TCR-β chains, in the region of the disulphide bonds, respectively. They were comparable in efficacy and complement theoretical expectations that they should have similar effects (assuming similar levels of uptake by T-cells, etc.).

Peptide O was an extension of core peptide and included sequences from the carboxyl terminus of the TCR-α a chain in the intracellular domain. Peptide O was most effective at ameliorating the development of MTB-induced arthritis and suggests that other downstream sequences from the core peptide may be important in influencing cell function. The core peptide is the smallest component of these sequences.

(iii) Examination of Peptides N, M and P

Methods. Rats received 1 mg of MTB in 0.2 ml squalane with or without peptides (7 mg). Single sites were used as noted above. Two of the control MTB rats developed arthritis early, two late, and one of the five remained well. This is consistent with the experimental model of 80% of MTB treated rats developing arthritis.

Results. (1) Weight. FIG. 8 shows the mean weight of each group.

(2) Ankle thickness. FIG. 9(a–d) demonstrates the extent of ankle involvement in these groups. Results of paw thickness were similar to ankle thickness. All five of the rats that were treated with Peptide N showed no symptoms of arthritis for the duration of the experiment (FIG. 9c). Rats that received Peptide M eventually had 2 of the group killed, on days 19 and 21, i.e, late in the experiment. One rat remained symptom-free. Two other rats had mild disease which resolved during the experiment. Of the 5 rats treated with Peptide P, one did not develop any symptoms, while the remaining four developed minor symptoms, some of which did not appear until late in the experiment. The symptoms did not constitute acute arthritis and the animals were not sacrificed. There is the clear suggestion from the graphs of paw and ankle thickness that the early development of symptoms was prolonged and severity decreased in the peptide treated groups. Discussion. The untreated controls developed active arthritis and were clearly the worst group. Peptide M, P and N were protective to a variable extent.

(iv) Experiment with Peptide L

Methods. Same as above. Each rat was injected intradermally, at the base of the tail, using a 21 gauge needle, with 1 mg MTB in 200 µl squalane, with or without 7 mg of peptide L suspended in this volume. A glass syringe was used.

Results. (i) Weight. All of the control MTB group developed arthritis and had to be sacrificed by day 18 (FIG. 10). By contrast none of the peptide L treated group lost weight. Rat 12 died from an anaesthetic cause.

(ii) Joint involvement. Both paw and ankle thickness were significantly decreased compared to control FIG. 11(a–d).

SUMMARY

Primary T-cells from MTB-sensitised rats were used to test peptides. This was immediately successful and CP inhibited 3H-thymidine uptake. Results were consistent and repeatable, whether PLNC or in vitro propagated T-cell lines were used. CP was most effective followed by peptides P and H. It must be remembered that results in vitro are biased in favour of the more soluble peptides.

Adjuvant induced arthritis model. Table 4 summarises in vivo experiments which favours effectiveness of the peptides tested. Peptide J, O, N and L were very effective in the induction of disease. Similarly peptide K, M and P has a variable response in the delay of disease induction and severity.

TABLE 4

Summary of in vivo adjuvant induced arthritis results

| PEPTIDE | CONTROL | TREATMENT |
|---|---|---|
| J | 8/10 | 3/10* |
| K | " | 5/10 |
| O | " | 1/10* |
| L | 5/5 | 0/5* |
| N | 4/5 | 0/5* |
| M | " | 2/5 |
| P | " | 0/5 (4 developed minor symptoms) |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Clevers, H., Alarcon, B., Wileman, T. & Terhorst, C. The T cell receptor/CD3 complex: A dynamic protein ensemble. Ann Rev Immunol. 6, 629–662, (1988)
2. Manolios, N., Bonifacino, J. S., & Klausner, R. D. Transmembrane helical interactions and the assembly of the T cell antigen receptor complex. Science, 248, 274–277, (1990)
3. Manolios N., Letourner F., Bonifacino J. S., & Klausner R. D. Pairwise, cooperative, and inhibitory interactions describe the assembly and probable structure of the T-cell antigen receptor. EMBO J. 10, 1643–1651, (1991)
4. Manolios, N., Kemp, O. & Li. Z. G. The T-cell antigen receptor alpha and beta chains interact via distinct regions with CD3 chains. Eur. J. Immunol. 24, 84–89 (1994).
5. PCT/AU96/00018 (WO 96/22306)—"Novel peptide" (Northern Sydney Area Health Service).
6. McQueen F M. The use of biologics in the treatment of rheumatoid arthritis (RA)—the good news and the bad news. Aust N Z J Med 1997; 27, 175–184.
7. Gaston J S H, Strober S, Solovera J J, et al: Dissection of mechanisms of immune injury in rheumatoid arthritis using total lymphoid irradiation. Arthritis and Rheum; 47: 127–33, (1988)
8. Paulus H E, Machleder H I, Levine S, Yu D T Y, MacDonald N S: Lymphocyte involvement in rheumatoid arthritis-studies during thoracic duct drainage. Arthritis Rheum: 20: 1249–62, (1977)
9. Emery P, Smith G N, Panayi G S: Lymphocytapheresis—a feasible treatment for rheumatoid arthritis. Brit J Rheum; 25: 40–43, (1986)
10. Watts R A, Isaacs J D: Immunotherapy of rheumatoid arthritis. Ann Rheum Dis; 51: 577–579, (1992)
11. Lipsky P E: Immunopathogenesis and treatment of rheumatoid arthritis. J Rheumatol; 19: 92–94, (1992)
12. Olsen N J, Cush J J, Lipsky P E et al. Multicentre trial of an anti-CD5 immunoconjugate in rheumatoid arthritis. Arthritis Rheum. 37 (Sup):S295, (1994)
13. Matteson E L, Yocum D E, St Clair W E et al., Treatment of active refractory rheumatoid arthritis with humanised monoclonal antibody CAMPATH-1H administered by daily subcutaneous injection. Arthritis Rheum; 38, 1187–93, (1995)
14. Moreland L W, Bucy R P, Tilden A et al. Use of a chimeric monoclonal anti-CD4 antibody in patients with refractory rheumatoid arthritis. Arthritis Rheum; 307–18, (1993)
15. van der Lubbe P A, Dijkmans B A C, Markusse H M, Nassander U, Breedveld F C. A randomised, double-blind, placebo controlled study of CD4 monoclonal antibody therapy in early rheumatoid arthritis. Arthritis Rheum. 38, 1097–106, (1995)
16. Moreland L W, Sewell K L, Trentham D E et al. Interleukin-2 diptheria fusion protein (DAB486IL-2) in refractory rheumatoid arthritis. A double-blind placebo-controlled trial with open-label extension. Arthritis Rheum; 1176–86, (1995)
17. Sewell K L, Moreland L W, Cush J J, Furst D E, Woodworth T F, Meehan R T. Phase I/II double blind dose response trial of a second fusion toxin DAB (389) IL-2 in rheumatoid arthritis. Arthritis Rheum. 36; S130, (1993)
18. Kingsley G, Pitzalis C, Panayi G S: Immunogenetic and cellular immune mechanisms in rheumatoid arthritis: Relevance to new therapeutic strategies. Brit J Rheum; 29: 58–64, (1990)
19. Altoroni R, Teitelbaum D, Arnon R, Puri J: Immunomodulation of experimental autoimmune encephalitis by antibodies to the antigen-Ia complex. Nature; 351: 147–150, (1991)
20. Rosenbaum J T, Adelman N E, McDevitt H O: In vivo effects of antibodies to immune response gene products. I. Haplotype-specific suppression of humoral responses with a monoclonal anti-Ia. J Exp Med; 154: 1694–98, (1981)
21. Steinman L, Rosenbaum J T, Srinam S, McDevitt HO: In vivo effects of antibodies to immune response gene products: Prevention of experimental allergic encephalomyelitis. Proc Natl Acad Sci USA; 78: 7111–14, (1981)
22. Quagliata F, Schenkelaars E J, Ferrone S. Immunotherapeutic approach to rheumatoid arthritis with anti-idiotypic antibodies to HLA-DR4. Isr J Med Sci; 29, 154–9, (1993)
23. Magistris M T, Alexander J, Coggeshall M, Altman M, et al: Antigen analog major histocompatibility complexes act as antagonists of the T-cell receptor. Cell; 68: 625–634, (1992)
24. Howell M D, Winters S T, Olee T, Powell H C, Carlo D J, et al: Vaccination against experimental allergic encephalomyelitis with T-cell receptor peptides. Science 1989; 246: 668–670.
25. Vanderbark A A, Hashim G A, Offner H: Immunization with a synthetic T-cell receptor V-region peptide protects against experimental autoimmune encephalomyelitis. Nature; 345: 541–544, (1989)
26. Stamenkovic I, Stegagno M, Wright K A, Krane S M, Amento E P, et al: Clonal dominance among T lymphocyte infiltrates in arthritis. Proc Natl Acad Sci USA; 85: 1179–1183, (1988)
27. Paliard X, West S G, Lafferty J A, Clements J. R, Kappler J W, et al: Evidence for the effects of a superantigen in rheumatoid arthritis. Science; 253; 325–329, (1991)
28. Feldmann M, Brennan F M, Chantry D, Haworth C, Turner M, et al: Cytokine production in the rheumatoid joint: implications for treatment. Ann Rheum Dis; 49: 480–486, (1990)
29. Elliott M J, Maini R N, Feldmann M et al., Randomsed double-blind comparison of chimeric monoclonal antibody to tumour necrosis factor a(cA2) versus placebo in rheumatoid arthritis. Lancet; 344, 1105–1-, (1994)
30. Rankin E C C, Choy E H S, Kassimos D et al. The therapeutic effects of an engineered human anti-tumour necrosis factor alpha antibody (CDP571) in rheumatoid arthritis. Br J Rheumatol; 34, 334–42, (1995).
31. Kyle V, Coughlan R J, Tighe H, Waldmann H, Hazleman B L: Beneficial effect of monoclonal antibody to interleukin 2 receptor on activated T-cells in rheumatoid arthritis. Ann Rheum Dis; 48:428–429, (1989)
32. Dower S K, Sims J E: Molecular characterisation of cytokine receptors. Ann Rheum Dis: 49: 452–459, (1990)
33. Moreland L W, Margolies G R, Heck L W et al. Soluble tumour necrosis factor receptor (sTNFR): Results of a phase I dose-escalation study in patients with rheumatoid arthritis. Arthritis Rheum; (Suppl) 37. S295, (1994)
34. McCune W J, Bayliss G E: Immunosupressive therapy for rheumatic disease. Curr Opin Rheumatol; 3: 355–362, (1991)
35. Manolios, N., Collier, S., Taylor, J., Pollard, J., Harrison, L., Bender, V. Immunomodulatory antigen receptor transmembrane peptides and their effect on T-cell mediated disease. Nature Medicine, 3, 84–87, (1997)
36. Samelson, L. E., O'Shea, J. J., Luong, H., Ross, P., Urdahl, K. B., Klausner, R. D., & Bluestone, J. T-cell antigen phosphorylation induced by an anti-receptor antibody. J. Immunol, 139, 2708–14 (1987)
37. Sedgwick J, McPhee I A M, Puklavec M. Isolation of encephalitogenic CD4+ T cell clones in the rat: Cloning methodology and IFN-g secretion. J. Immunol Methods, 121: 185–196, (1989).

What is claimed is:

1. A peptide that inhibits T-cell antigen receptor (TCR) function, which has a formula selected from the group consisting of formula NH2-Ile-Leu-Leu-Leu-Lys-Val-Ala-Gly-Phe-OH (SEQ ID NO. 6), NH2-Ile-Leu-Leu-Leu-Lys-Val-Ala-Gly-OH (SEQ ID NO. 7), NH2-Leu-Arg-Ile-Leu-Leu-Leu-Gly-Val-OH (SEQ ID NO. 8), NH2-Leu-Gly-Ile-Leu-Leu-Leu-Lys-Val-OH (SEQ ID NO. 9), NH2-Ile-Leu-Leu-Gly-Lys-Ala-Thr-Leu-Tyr-OH (SEQ ID NO. 10), NH2-Met-Gly-Leu-Arg-Ile-Leu-Leu-Leu-OH (SEQ ID NO. 11), NH2-Leu-Leu-Met-Thr-Leu-Arg-Leu-Trp-Ser-Ser-COOH (SEQ ID NO. 12)

NH2-Ile-Ile-Val-Thr-Asp-Val-Ile-Ala-Thr-Leu-OH (SEQ ID NO. 13)

NH2-Ile-Val-Ile-Val-Asp-Ile-Cys-Ile-Thr-OH (SEQ ID NO. 14),

NH2-Phe-Leu-Phe-Ala-Glu-Ile-Val-Ser-Ile-OH (SEQ ID NO. 15)

NH2-Ala-Gly-Phe-Asn-Leu-Leu-Met-Thr-COOH (SEQ ID NO. 16).

2. A peptide which inhibits TCR function, wherein the peptide has the formula

NH2-Ile-Ile-Val-Thr-Asp-Val-Ile-Ala-Thr-Leu-OH (SEQ ID NO. 13),

NH2-Ile-Val-Ile-Val-Asp-Ile-Cys-Ile-Thr-OH (SEQ ID NO. 14), or

NH2-Phe-Leu-Phe-Ala-Glu-Ile-Val-Ser-Ile-OH (SEQ ID NO. 15).

3. A peptide which inhibits TCR function, wherein the peptide is derived from the TCR-α intracellular chain and comprises the formula:

NH2-Ala-Gly-Phe-Asn-Leu-Leu-Met-Thr-COOH (SEQ ID NO. 16).

4. A peptide which inhibits T-Cell antigen receptor function wherein the peptide has the formula:

NH2-Tyr-Gly-Arg-Ala-Asp-Cys-Gly-Ile-Thr-Ser-OH (SEQ ID NO. 17), or

NH2-Trp-Gly-Arg-Ala-Asp-Cys-Gly-Ile-Thr-Ser-OH (SEQ ID NO. 18), or

NH2-Tyr-Gly-Arg-Ala-Asp-Cys-Ile-Thr-Ser-OH (SEQ ID NO. 19), or

NH2-Ser-Ser-Asp-Val-Pro-Cys-Asp-Ala-Thr-Leu-Thr-OH (SEQ ID NO. 20).

5. The peptide according to claim 1 which has the formula:

NH2-Ile-Leu-Leu-Leu-Lys-Val-Ala-Gly-Phe-OH (SEQ ID NO. 6),

NH2-Ile-Leu-Leu-Leu-Lys-Val-Ala-Gly-OH (SEQ ID NO. 7),

NH2-Leu-Arg-Ile-Leu-Leu-Leu-Gly-Val-OH (SEQ ID NO. 8),

NH2-Leu-Gly-Ile-Leu-Leu-Leu-Lys-Val-OH (SEQ ID NO. 9),

NH2-Ile-Leu-Leu-Gly-Lys-Ala-Thr-Leu-Tyr-OH (SEQ ID NO. 10),

NH2-Met-Gly-Leu-Arg-Ile-Leu-Leu-Leu-OH (SEQ ID NO. 11), or

NH2-Leu-Leu-Met-Thr-Leu-Arg-Leu-Trp-Ser-Ser-COOH (SEQ ID NO. 12).

6. A therapeutic composition comprising a peptide as claimed in claim 1, and a pharmaceutically acceptable carrier.

7. A method of treating a subject suffering from a condition selected from the group consisting of rheumatoid arthritis, inflammatory bowel disease, psoriasis, inflammatory conditions, myositis, and ankylosing spondylitis, the method comprising the step of administering an effective amount of a composition as claimed in claim 6 to the subject.

8. A method according to claim 7, in which the condition is rheumatoid arthritis or psoriasis.

* * * * *

SEQUENCE LISTING

```
<160> NUMBER OF SEQ ID NOS: 26

<210> SEQ ID NO 1
<211> LENGTH: 23
<212> TYPE: PRT
<213> ORGANISM: Mus musculus

<400> SEQUENCE: 1

Asn Leu Ser Val Met Gly Leu Arg Ile Leu Leu Leu Lys Val Ala Gly
 1               5                  10                  15

Phe Asn Leu Leu Met Thr Leu
            20

<210> SEQ ID NO 2
<211> LENGTH: 23
<212> TYPE: PRT
<213> ORGANISM: Rattus rattus

<400> SEQUENCE: 2

Asn Leu Ser Val Met Gly Leu Arg Ile Leu Leu Leu Lys Val Ala Gly
 1               5                  10                  15

Phe Asn Leu Leu Met Thr Leu
            20

<210> SEQ ID NO 3
<211> LENGTH: 23
<212> TYPE: PRT
<213> ORGANISM: Ovis aries

<400> SEQUENCE: 3

Asn Leu Ser Val Thr Val Phe Arg Ile Leu Leu Leu Lys Val Val Gly
 1               5                  10                  15

Phe Asn Leu Leu Met Thr Leu
            20

<210> SEQ ID NO 4
```

```
<211> LENGTH: 23
<212> TYPE: PRT
<213> ORGANISM: Bos taurus

<400> SEQUENCE: 4

Asn Leu Ser Val Ile Val Phe Arg Ile Leu Leu Lys Val Val Gly
 1               5                  10                  15

Phe Asn Leu Leu Met Thr Leu
             20

<210> SEQ ID NO 5
<211> LENGTH: 23
<212> TYPE: PRT
<213> ORGANISM: Homo sapiens

<400> SEQUENCE: 5

Asn Ser Leu Val Ile Gly Phe Arg Ile Leu Leu Leu Lys Val Ala Gly
 1               5                  10                  15

Phe Asn Leu Leu Met Thr Leu
             20

<210> SEQ ID NO 6
<211> LENGTH: 9
<212> TYPE: PRT
<213> ORGANISM: Homo sapiens

<400> SEQUENCE: 6

Ile Leu Leu Leu Lys Val Ala Gly Phe
 1               5

<210> SEQ ID NO 7
<211> LENGTH: 8
<212> TYPE: PRT
<213> ORGANISM: Homo sapiens

<400> SEQUENCE: 7

Ile Leu Leu Leu Lys Val Ala Gly
 1               5

<210> SEQ ID NO 8
<211> LENGTH: 8
<212> TYPE: PRT
<213> ORGANISM: Homo sapiens

<400> SEQUENCE: 8

Leu Arg Ile Leu Leu Leu Gly Val
 1               5

<210> SEQ ID NO 9
<211> LENGTH: 8
<212> TYPE: PRT
<213> ORGANISM: Homo sapiens

<400> SEQUENCE: 9

Leu Gly Ile Leu Leu Leu Lys Val
 1               5

<210> SEQ ID NO 10
<211> LENGTH: 9
<212> TYPE: PRT
<213> ORGANISM: Homo sapiens

<400> SEQUENCE: 10

Ile Leu Leu Gly Lys Ala Thr Leu Tyr
```

-continued

```
<210> SEQ ID NO 11
<211> LENGTH: 8
<212> TYPE: PRT
<213> ORGANISM: Homo sapiens

<400> SEQUENCE: 11

Met Gly Leu Arg Ile Leu Leu Leu
  1               5

<210> SEQ ID NO 12
<211> LENGTH: 10
<212> TYPE: PRT
<213> ORGANISM: Homo sapiens

<400> SEQUENCE: 12

Leu Leu Met Thr Leu Arg Leu Trp Ser Ser
  1               5                  10

<210> SEQ ID NO 13
<211> LENGTH: 10
<212> TYPE: PRT
<213> ORGANISM: Homo sapiens

<400> SEQUENCE: 13

Ile Ile Val Thr Asp Val Ile Ala Thr Leu
  1               5                  10

<210> SEQ ID NO 14
<211> LENGTH: 9
<212> TYPE: PRT
<213> ORGANISM: Homo sapiens

<400> SEQUENCE: 14

Ile Val Ile Val Asp Ile Cys Ile Thr
  1               5

<210> SEQ ID NO 15
<211> LENGTH: 9
<212> TYPE: PRT
<213> ORGANISM: Homo sapiens

<400> SEQUENCE: 15

Phe Leu Phe Ala Glu Ile Val Ser Ile
  1               5

<210> SEQ ID NO 16
<211> LENGTH: 8
<212> TYPE: PRT
<213> ORGANISM: Homo sapiens

<400> SEQUENCE: 16

Ala Gly Phe Asn Leu Leu Met Thr
  1               5

<210> SEQ ID NO 17
<211> LENGTH: 10
<212> TYPE: PRT
<213> ORGANISM: Homo sapiens

<400> SEQUENCE: 17

Tyr Gly Arg Ala Asp Cys Gly Ile Thr Ser
  1               5                  10
```

```
<210> SEQ ID NO 18
<211> LENGTH: 10
<212> TYPE: PRT
<213> ORGANISM: Homo sapiens

<400> SEQUENCE: 18

Trp Gly Arg Ala Asp Cys Gly Ile Thr Ser
 1               5                  10

<210> SEQ ID NO 19
<211> LENGTH: 9
<212> TYPE: PRT
<213> ORGANISM: Homo sapiens

<400> SEQUENCE: 19

Tyr Gly Arg Ala Asp Cys Ile Thr Ser
 1               5

<210> SEQ ID NO 20
<211> LENGTH: 11
<212> TYPE: PRT
<213> ORGANISM: Homo sapiens

<400> SEQUENCE: 20

Ser Ser Asp Val Pro Cys Asp Ala Thr Leu Thr
 1               5                  10

<210> SEQ ID NO 21
<211> LENGTH: 9
<212> TYPE: PRT
<213> ORGANISM: Homo sapiens

<400> SEQUENCE: 21

Gly Leu Arg Ile Leu Leu Leu Lys Val
 1               5

<210> SEQ ID NO 22
<211> LENGTH: 8
<212> TYPE: PRT
<213> ORGANISM: Homo sapiens

<400> SEQUENCE: 22

Met Gly Leu Arg Ile Leu Leu Leu
 1               5

<210> SEQ ID NO 23
<211> LENGTH: 8
<212> TYPE: PRT
<213> ORGANISM: Homo sapiens

<400> SEQUENCE: 23

Leu Lys Ile Leu Leu Leu Arg Val
 1               5

<210> SEQ ID NO 24
<211> LENGTH: 8
<212> TYPE: PRT
<213> ORGANISM: Homo sapiens

<400> SEQUENCE: 24

Leu Asp Ile Leu Leu Leu Glu Val
 1               5

<210> SEQ ID NO 25
```

```
-continued

<211> LENGTH: 9
<212> TYPE: PRT
<213> ORGANISM: Homo sapiens

<400> SEQUENCE: 25

Leu Arg Ile Leu Leu Leu Ile Lys Val
  1               5

<210> SEQ ID NO 26
<211> LENGTH: 7
<212> TYPE: PRT
<213> ORGANISM: Homo sapiens

<400> SEQUENCE: 26

Leu Arg Leu Leu Leu Lys Val
  1               5
```